United States Patent [19]
Kimachi et al.

[11] Patent Number: 5,760,185
[45] Date of Patent: Jun. 2, 1998

[54] ANTI-FELINE HERPES VIRUS-1 RECOMBINANT ANTIBODY AND GENE FRAGMENT CODING FOR SAID ANTIBODY

[75] Inventors: Kazuhiko Kimachi; Hiroaki Maeda, both of Kumamoto; Kiyoto Nishiyama, Kikuchi; Sachio Tokiyoshi, Kumamoto, all of Japan

[73] Assignee: Juridical Foundation The Chemo-Sero-Therapeutic Research Institute, Kumamoto, Japan

[21] Appl. No.: 436,463

[22] PCT Filed: Nov. 25, 1993

[86] PCT No.: PCT/JP93/01724

§ 371 Date: May 26, 1995

§ 102(e) Date: May 26, 1995

[87] PCT Pub. No.: WO94/12661

PCT Pub. Date: Sep. 6, 1994

[30] Foreign Application Priority Data

Nov. 28, 1992 [JP] Japan .................................. 4-341255

[51] Int. Cl.$^6$ .......................... C07K 16/00; C12P 21/08; A61K 38/00; A61K 39/395
[52] U.S. Cl. ........................ 530/387.3; 530/388.1; 530/388.3; 530/324; 424/133.1; 424/147.1; 424/800; 424/809; 424/801
[58] Field of Search ................. 530/387.3, 388.1, 530/388.3, 324, 386; 424/133.1, 199.1, 147.1, 800, 801, 809

[56] References Cited

FOREIGN PATENT DOCUMENTS

| 0417486 | 3/1991 | Japan . |
| 3072873 | 5/1991 | Japan . |
| 3123486 | 5/1991 | Japan . |
| 3201986 | 9/1991 | Japan . |

OTHER PUBLICATIONS

Limcumpao et al. (A) Jap. J. of Veterinary Sci. 52(2): 351–359, 1990.
Horimoto et al. Arch. of Virol. 111:127–132, 1990.
Limcumpao et al (B) J. Veterinary Medical Sci. 53(3): 423–432, 1991.
Limcumpao et al (C) Arch. of Virol. 111:165–176, 1990
Buckel et al. Gene 51:13–19, 1987.

Primary Examiner—Marian C. Knode
Assistant Examiner—Jay F. Williams
Attorney, Agent, or Firm—Browdy and Neimark

[57] ABSTRACT

An anti-FHV-1 recombinant antibody efficacious for treatment, prevention and diagnosis of feline herpes virus-1 (FHV-1) and a gene fragment useful for preparing the same are provided. A cell producing a mouse monoclonal antibody having an excellent neutralizing activity against FHV-1 was constructed, and a gene fragment coding for V region of said antibody responsible for the specific binding activity against FHV-1 was obtained. Using this gene fragment and a gene fragment coding for the constant region of a feline antibody, a chimeric anti-FHV-1 recombinant antibody is obtained.

18 Claims, 11 Drawing Sheets

1. MOLECULAR WEIGHT MARKER
2. ANTI-FHV H CHAIN GENE
3. ANTI-FHV L CHAIN GENE

FIG. 2

```
                                            TCTAGAAGCTTGCCGCCACC
                                                  HindIII
                                                                60
  Leader                                                     | FR1
MetGlyArgLeuThrPheSerPheLeuLeuLeuIleValProAlaTyrValLeuSerGln
ATGGGCAGACTTACATTCTCATTCCTGCTACTGATTGTCCCTGCATATGTCCTGTCCCAG
    (MHL341)

FR1                                             120
ValThrLeuLysGluSerGlyProGlyIleLeuGlnProSerGlnThrLeuSerLeuThr
GTTACTCTGAAAGAGTCTGGCCCTGGGATATTGCAGCCCTCCCAGACCCTCAGTCTGACT

FR1         |         CDR1           | FR2           180
CysSerPheSerGlyPheSerLeuSerThrSerGlyMetGlyAlaGlyTrpIleArgGln
TGTTCTTTCTCTGGGTTTTCACTGAGCACTTCTGGTATGGGTGCAGGCTGGATTCGTCAG

FR2                |           CDR2              240
ProSerGlyLysGlyLeuGluTrpLeuAlaHisIleTrpTrpAspAspValLysArgTyr
CCATCAGGGAAGGGTCTGGAGTGGCTGGCACACATTTGGTGGGATGATGTCAAGCGCTAT

CDR2           |               FR3                 300
AsnProAlaLeuLysSerArgLeuThrIleSerLysAspThrSerSerSerGlnValPhe
AACCCAGCCCTGAAGAGCCGACTGACTATCTCCAAGGATACCTCCAGCAGCCAGGTATTC

FR3                              | CDR3  360
LeuLysIleAlaSerValAspThrAlaAspThrAlaThrTyrPheCysValArgSerGln
CTCAAGATCGCCAGCGTGGACACTGCAGATACTGCCACATATTTTTGTGTTCGATCCCAG

CDR3                  |            FR4            420
IleTyrPheAspTyr|AspGlyAlaTrpPhe|ProPheTrpGlyGlnGlyThrLeuValThr
ATCTACTTTGATTACGACGGGGCCTGGTTTCCTTTCTGGGGCCAAGGGACTCTGGTCACT

ValSerAla
GTCTCTGCAGGTGAGTGGATCC
  (MJH3)         BamHI
```

FIG. 3

```
                                    GGAATTCAAGCTTGCCGCCACC
                                          HindIII (MKL104)
| Leader                                                    60
MetValSerThrAlaGlnPheLeuGlyLeuMetLeuPheTrpIleSerAlaSerArgGly
ATGGTATCCTCACCTCAGTTCCTTGGACTTATGCTTTTTTGGATTTCAGCCTCCAGAGGT

|              FR1                                         120
AspIleValLeuThrGlnSerProAlaThrLeuSerValThrProGlyAspSerValSer
GATATTGTGCTAACTCAGTCTCCAGCCACCCTGTCTGTGACTCCAGGAGATAGCGTCAGT

FR1  |          CDR1              |         FR2     180
LeuSerCysArgAlaSerGlnSerIleSerAsnAsnLeuHisTrpTyrGlnGlnLysSer
CTTTCCTGCAGGGCCAGCCAAAGTATTAGCAACAACCTACACTGGTATCAACAAAAATCA

FR2            ·    |    CDR2      |   FR3     240
HisGluSerProArgLeuLeuIleLysTyrAlaSerGlnSerIleSerGlyIleProSer
CATGAGTCTCCAAGGCTTCTCATCAAGTATGCTTCCCAGTCCATCTCTGGGATCCCCTCC

FR3                             300
ArgPheSerGlySerGlySerGlyThrAspPheThrLeuSerIleAsnSerValGluThr
AGGTTCAGTGGCAGTGGATCAGGGACAGATTTCACTCTCAGTATCAACAGTGTGGAGACT

FR3              |       CDR3           | FR4  360
GluAspPheGlyMetTyrPheCysGlnGlnSerAsnSerTrpProHisThrPheGlyAla
GAAGATTTTGGAATGTATTTCTGTCAACAGAGTAACAGCTGGCCTCACACGTTCGGTGCT

FR4
GlyThrLysLeuGluLeuLys
GGGACCAAGCTGGAGCTGAAACGTAAGTGGATCCAGATCTAG
        (MJK124)                  BamHI
```

FIG. 4

```
              |  Leader                    |          FR1              |      CDR1     | FR2  60
      JH2     MGRLTFSFLLLIVPAYVLSQVTLKESGPGILQPSQTLSLTCSFSGFSLSTSGMGAGWIRQ

***************************** . ****
ANTIBODY 1                                 DVQHISFQVTLKESGPGILQPSQTLSLTCSFSGFSLSTSGMGVSWIRQ

************************ . *****
ANTIBODY 2                                            PGILQPSQTLSLTCSFSGFSLSTSGMGVGWIRQ

*********************** . *****
ANTIBODY 3                                             GILQPSQTLSLTCSFSGFSLSTSGMGVGWIRQ

************************ . ****
ANTIBODY 4                                           PGILQPSQTLSLTCSFSGFSLSTSGMG-SWIRQ

FR2       |    CDR2         |              FR3                    | CDR3
      JH2     PSGKGLEWLAHIWWDDVKRYNPALKSRLTISKDTSSQVFLKIASVDTADTATYFCVRSQ

***********.***  *****.****************..*****.*********** .*.*..
ANTIBODY 1    PSGKGLEWLAHIYWDDDKRYNPSLKSRLTISKDTSRNQVFLKITSVDTADTATYYCARRE

***************  *******************.**************.**.*.*.
ANTIBODY 2    PSGKGLEWLAHIWWDDDKRYNPALKSRLTISKDTSSNQVFLKIASVDTADTSTYYCARDW

***************  *******************.** .************ .*.*.
ANTIBODY 3    PSGKGLEWLAHIWWDDDKRYNPALKSRLTISKDTSSNQVSLKIASVDTADTATYYCART-

***********.***  *****.****************..*****.*********.*.**
ANTIBODY 4    PSGKGLEWLAHIYWDDDKRYNPSLKSRLTISKDTSRNQVFLKITSVDTADTATYYCARSY

CDR3       | FR4    143
      JH2     -IYFDYDGAWFPFWGQGTLVTVSA

. *-----* . *****
ANTIBODY 1    -GGRSY-----FDYWGQGTT

.  ****         ***** . ***
ANTIBODY 2    -DYFDY-------WGQGTTLTVS

* . .  . * *  **.** *****.
ANTIBODY 3    YYYG-SSHWYFDVWGAGTTVTVSS

.. **  .      . *****
ANTIBODY 4    -GNGDYYAM--DYWGQGTS
```

FIG. 5

```
              | Leader                      | FR1                        | CDR1     | FR2  60
      JH2     MVSSAQFLGLMLFWISASRGDIVLTQSPATLSVTPGDSVSLSCRASQSISNNLHWYQQKS

**  ..*.***********************  ************************
ANTIBODY 1    MVFTPQILGLMLFWISASRGDIVLTQSPATLSVTPRDSVSLSCRASQSISNNLHWYQQKS

*******************************************
ANTIBODY 2                                    DIVLTQSPATLSVTPGDSVSLSCRASQSISNNLHWYQQKS

****************.***********.**********
ANTIBODY 3                                    DIVLTQSPATLSVTPGNSVSLSCRASQSIGNNLHWYQQKS

******************  ********************
ANTIBODY 4                                    IVLTQSPATLSVTPGDSV-LSCRASQSISNNLHWYQQKS

FR2     | CDR2 |                FR3                    | CDR3        120
      JH2     HESPRLLIKYASQSISGIPSRFSGSGSGTDFTLSINSVETEDFGMYFCQQSNSWPHTFGA

*******************************************************  ****
ANTIBODY 1    HESPRLLIKYASQSISGIPSRFSGSGSGTDFTLSINSVETEDFGMYFCQQSNSWPLTFGA

***********************************************************.
ANTIBODY 2    HESPRLLIKYASQSISGIPSRFSGSGSGTDFTLSINSVETEDFGMYFCQQSNSWPHTFGS

*********************************************************.***.
ANTIBODY 3    HESPRLLIKYASQSISGIPSRFSGSGSGTDFTLSINSVETEDFGMYFCQQSNSWPYTFGG

********.****** ***************** **.***************** **.*
ANTIBODY 4    HESPRLLINYASQSIS-IPSRFSGSGSGTDFTLIINNVETEDFGMYFCQQSNSWPLTFAA

FR4    127
      JH2     GTKLELK

*******
ANTIBODY 1    GTKLELK

ANTIBODY 2

*****.*
ANTIBODY 3    GTKLEIK

******
ANTIBODY 4    GTKLEL
```

1. ANTI-FHV CHIMERIC ANTIBODY (FH2)
2. FELINE POLYCLONAL IgG
3. MOLECULAR WEIGHT MARKER

5,760,185

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 462 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 21..449

( x i ) SEQUENCE DESCRIPTION: SEQ ID NO:1:

```
TCTAGAAGCT TGCCGCCACC ATG GGC AGA CTT ACA TTC TCA TTC CTG CTA          50
                       Met Gly Arg Leu Thr Phe Ser Phe Leu Leu
                        1               5                  10

CTG ATT GTC CCT GCA TAT GTC CTG TCC CAG GTT ACT CTG AAA GAG TCT        98
Leu Ile Val Pro Ala Tyr Val Leu Ser Gln Val Thr Leu Lys Glu Ser
             15                  20                  25
```

```
GGC CCT GGG ATA TTG CAG CCC TCC CAG ACC CTC AGT CTG ACT TGT TCT      146
Gly Pro Gly Ile Leu Gln Pro Ser Gln Thr Leu Ser Leu Thr Cys Ser
            30                  35                  40

TTC TCT GGG TTT TCA CTG AGC ACT TCT GGT ATG GGT GCA GGC TGG ATT      194
Phe Ser Gly Phe Ser Leu Ser Thr Ser Gly Met Gly Ala Gly Trp Ile
            45                  50                  55

CGT CAG CCA TCA GGG AAG GGT CTG GAG TGG CTG GCA CAC ATT TGG TGG      242
Arg Gln Pro Ser Gly Lys Gly Leu Glu Trp Leu Ala His Ile Trp Trp
        60                  65                  70

GAT GAT GTC AAG CGC TAT AAC CCA GCC CTG AAG AGC CGA CTG ACT ATC      290
Asp Asp Val Lys Arg Tyr Asn Pro Ala Leu Lys Ser Arg Leu Thr Ile
75                  80                  85                  90

TCC AAG GAT ACC TCC AGC AGC CAG GTA TTC CTC AAG ATC GCC AGC GTG      338
Ser Lys Asp Thr Ser Ser Ser Gln Val Phe Leu Lys Ile Ala Ser Val
                95                  100                 105

GAC ACT GCA GAT ACT GCC ACA TAT TTT TGT GTT CGA TCC CAG ATC TAC      386
Asp Thr Ala Asp Thr Ala Thr Tyr Phe Cys Val Arg Ser Gln Ile Tyr
            110                 115                 120

TTT GAT TAC GAC GGG GCC TGG TTT CCT TTC TGG GGC CAA GGG ACT CTG      434
Phe Asp Tyr Asp Gly Ala Trp Phe Pro Phe Trp Gly Gln Gly Thr Leu
        125                 130                 135

GTC ACT GTC TCT GCA GGTGAGTGGA TCC                                    462
Val Thr Val Ser Ala
140
```

(2) INFORMATION FOR SEQ ID NO:2:

(i) SEQUENCE CHARACTERISTICS:
        (A) LENGTH: 143 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Arg Leu Thr Phe Ser Phe Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
            35                  40                  45

Ser Thr Ser Gly Met Gly Ala Gly Trp Ile Arg Gln Pro Ser Gly Lys
        50                  55                  60

Gly Leu Glu Trp Leu Ala His Ile Trp Trp Asp Asp Val Lys Arg Tyr
65                  70                  75                  80

Asn Pro Ala Leu Lys Ser Arg Leu Thr Ile Ser Lys Asp Thr Ser Ser
                85                  90                  95

Ser Gln Val Phe Leu Lys Ile Ala Ser Val Asp Thr Ala Asp Thr Ala
            100                 105                 110

Thr Tyr Phe Cys Val Arg Ser Gln Ile Tyr Phe Asp Tyr Asp Gly Ala
            115                 120                 125

Trp Phe Pro Phe Trp Gly Gln Gly Thr Leu Val Thr Val Ser Ala
        130                 135                 140
```

(2) INFORMATION FOR SEQ ID NO:3:

(i) SEQUENCE CHARACTERISTICS:
        (A) LENGTH: 424 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 23..403

(xi) SEQUENCE DESCRIPTION: SEQ ID NO:3:

```
GGAATTCAAG CTTGCCGCCA CC ATG GTA TCC TCA CCT CAG TTC CTT GGA CTT        52
                         Met Val Ser Ser Pro Gln Phe Leu Gly Leu
                             145                 150

ATG CTT TTT TGG ATT TCA GCC TCC AGA GGT GAT ATT GTG CTA ACT CAG        100
Met Leu Phe Trp Ile Ser Ala Ser Arg Gly Asp Ile Val Leu Thr Gln
    155                 160                 165

TCT CCA GCC ACC CTG TCT GTG ACT CCA GGA GAT AGC GTC AGT CTT TCC        148
Ser Pro Ala Thr Leu Ser Val Thr Pro Gly Asp Ser Val Ser Leu Ser
170                 175                 180                 185

TGC AGG GCC AGC CAA AGT ATT AGC AAC AAC CTA CAC TGG TAT CAA CAA        196
Cys Arg Ala Ser Gln Ser Ile Ser Asn Asn Leu His Trp Tyr Gln Gln
                190                 195                 200

AAA TCA CAT GAG TCT CCA AGG CTT CTC ATC AAG TAT GCT TCC CAG TCC        244
Lys Ser His Glu Ser Pro Arg Leu Leu Ile Lys Tyr Ala Ser Gln Ser
                205                 210                 215

ATC TCT GGG ATC CCC TCC AGG TTC AGT GGC AGT GGA TCA GGG ACA GAT        292
Ile Ser Gly Ile Pro Ser Arg Phe Ser Gly Ser Gly Ser Gly Thr Asp
                220                 225                 230

TTC ACT CTC AGT ATC AAC AGT GTG GAG ACT GAA GAT TTT GGA ATG TAT        340
Phe Thr Leu Ser Ile Asn Ser Val Glu Thr Glu Asp Phe Gly Met Tyr
            235                 240                 245

TTC TGT CAA CAG AGT AAC AGC TGG CCT CAC ACG TTC GGT GCT GGG ACC        388
Phe Cys Gln Gln Ser Asn Ser Trp Pro His Thr Phe Gly Ala Gly Thr
250                 255                 260                 265

AAG CTG GAG CTG AAA CGTAAGTGGA TCCAGATCTA G                            424
Lys Leu Glu Leu Lys
                270
```

(2) INFORMATION FOR SEQ ID NO:4:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO:4:

```
Met Val Ser Ser Pro Gln Phe Leu Gly Leu Met Leu Phe Trp Ile Ser
 1               5                  10                  15

Ala Ser Arg Gly Asp Ile Val Leu Thr Gln Ser Pro Ala Thr Leu Ser
                20                  25                  30

Val Thr Pro Gly Asp Ser Val Ser Leu Ser Cys Arg Ala Ser Gln Ser
                35                  40                  45

Ile Ser Asn Asn Leu His Trp Tyr Gln Gln Lys Ser His Glu Ser Pro
            50                  55                  60

Arg Leu Leu Ile Lys Tyr Ala Ser Gln Ser Ile Ser Gly Ile Pro Ser
65                  70                  75                  80

Arg Phe Ser Gly Ser Gly Ser Gly Thr Asp Phe Thr Leu Ser Ile Asn
                    85                  90                  95

Ser Val Glu Thr Glu Asp Phe Gly Met Tyr Phe Cys Gln Gln Ser Asn
                100                 105                 110

Ser Trp Pro His Thr Phe Gly Ala Gly Thr Lys Leu Glu Leu Lys
                115                 120                 125
```

(2) INFORMATION FOR SEQ ID NO:5:

(i) SEQUENCE CHARACTERISTICS:
        (A) LENGTH: 1005 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..999
        (D) OTHER INFORMATION: /function=""
            / product= "k6"

(xi) SEQUENCE DESCRIPTION: SEQ ID NO:5:

```
ACC  ACG  GCC  CCA  TCG  GTG  TTC  CCA  CTG  GCC  CCC  AGC  TGC  GGG  ACC  ACA       48
Thr  Thr  Ala  Pro  Ser  Val  Phe  Pro  Leu  Ala  Pro  Ser  Cys  Gly  Thr  Thr
          130                      135                      140

TCT  GGC  GCC  ACC  GTG  GCC  CTG  GCC  TGC  CTG  GTG  TTA  GGC  TAC  TTC  CCT       96
Ser  Gly  Ala  Thr  Val  Ala  Leu  Ala  Cys  Leu  Val  Leu  Gly  Tyr  Phe  Pro
     145                      150                      155

GAG  CCG  GTG  ACC  GTG  TCC  TGG  AAC  TCC  GGC  GCC  CTG  ACC  AGC  GGT  GTG      144
Glu  Pro  Val  Thr  Val  Ser  Trp  Asn  Ser  Gly  Ala  Leu  Thr  Ser  Gly  Val
160                      165                      170                      175

CAC  ACC  TTC  CCG  GCC  GTC  CTG  CAG  GCC  TCG  GGG  CTG  TAC  TCT  CTC  AGC      192
His  Thr  Phe  Pro  Ala  Val  Leu  Gln  Ala  Ser  Gly  Leu  Tyr  Ser  Leu  Ser
                    180                      185                      190

AGC  ATG  GTG  ACA  GTG  CCC  TCC  AGC  AGG  TGG  CTC  AGT  GAC  ACC  TTC  ACC      240
Ser  Met  Val  Thr  Val  Pro  Ser  Ser  Arg  Trp  Leu  Ser  Asp  Thr  Phe  Thr
               195                      200                      205

TGC  AAC  GTG  GCC  CAC  CCG  CCC  AGC  AAC  ACC  AAG  GTG  GAC  AAG  ACC  GTG      288
Cys  Asn  Val  Ala  His  Pro  Pro  Ser  Asn  Thr  Lys  Val  Asp  Lys  Thr  Val
          210                      215                      220

CGC  AAA  ACA  GAC  CAC  CCA  CCG  GGA  CCC  AAA  CCC  TGC  GAC  TGT  CCC  AAA      336
Arg  Lys  Thr  Asp  His  Pro  Pro  Gly  Pro  Lys  Pro  Cys  Asp  Cys  Pro  Lys
     225                      230                      235

TGC  CCA  CCC  CCT  GAG  ATG  CTT  GGA  GGA  CCG  TCC  ATC  TTC  ATC  TTC  CCC      384
Cys  Pro  Pro  Pro  Glu  Met  Leu  Gly  Gly  Pro  Ser  Ile  Phe  Ile  Phe  Pro
240                      245                      250                      255

CCA  AAA  CCC  AAG  GAC  ACC  CTC  TCG  ATT  TCC  CGG  ACG  CCC  GAG  GTC  ACA      432
Pro  Lys  Pro  Lys  Asp  Thr  Leu  Ser  Ile  Ser  Arg  Thr  Pro  Glu  Val  Thr
                    260                      265                      270

TGC  TTG  GTG  GTG  GAC  TTG  GGC  CCA  GAT  GAC  TCC  GAT  GTC  CAG  ATC  ACA      480
Cys  Leu  Val  Val  Asp  Leu  Gly  Pro  Asp  Asp  Ser  Asp  Val  Gln  Ile  Thr
               275                      280                      285

TGG  TTT  GTG  GAT  AAC  ACC  CAG  GTG  TAC  ACA  GCC  AAG  ACG  AGT  CCG  CGT      528
Trp  Phe  Val  Asp  Asn  Thr  Gln  Val  Tyr  Thr  Ala  Lys  Thr  Ser  Pro  Arg
          290                      295                      300

GAG  GAG  CAG  TTC  AAC  AGC  ACC  TAC  CGT  GTG  GTC  AGT  GTC  CTC  CCC  ATC      576
Glu  Glu  Gln  Phe  Asn  Ser  Thr  Tyr  Arg  Val  Val  Ser  Val  Leu  Pro  Ile
     305                      310                      315

CTA  CAC  CAG  GAC  TGG  CTC  AAG  GGG  AAG  GAG  TTC  AAG  TGC  AAG  GTC  AAC      624
Leu  His  Gln  Asp  Trp  Leu  Lys  Gly  Lys  Glu  Phe  Lys  Cys  Lys  Val  Asn
320                      325                      330                      335

AGC  AAA  TCC  CTC  CCC  TCC  CCC  ATC  GAG  AGG  ACC  ATC  TCC  AAG  GCC  AAA      672
Ser  Lys  Ser  Leu  Pro  Ser  Pro  Ile  Glu  Arg  Thr  Ile  Ser  Lys  Ala  Lys
                    340                      345                      350

GGA  CAG  CCC  CAC  GAG  CCC  CAG  GTG  TAC  GTC  CTG  CCT  CCA  GCC  CAG  GAG      720
Gly  Gln  Pro  His  Glu  Pro  Gln  Val  Tyr  Val  Leu  Pro  Pro  Ala  Gln  Glu
               355                      360                      365

GAG  CTC  AGC  AGG  AAC  AAA  GTC  AGT  GTG  ACC  TGC  CTG  ATC  AAA  AGC  TTC      768
```

-continued

| | | | | | | | | | | | | | | | | |
|---|---|---|---|---|---|---|---|---|---|---|---|---|---|---|---|---|
| Glu | Leu | Ser | Arg | Asn | Lys | Val | Ser | Val | Thr | Cys | Leu | Ile | Lys | Ser | Phe | |
| | | 370 | | | | 375 | | | | | 380 | | | | | |

| CAC | CCG | CCT | GAC | ATT | GCC | GTC | GAG | TGG | GAG | ATC | ACC | GGA | CAG | CCG | GAG | 816 |
|---|---|---|---|---|---|---|---|---|---|---|---|---|---|---|---|---|
| His | Pro | Pro | Asp | Ile | Ala | Val | Glu | Trp | Glu | Ile | Thr | Gly | Gln | Pro | Glu | |
| 385 | | | | | 390 | | | | | 395 | | | | | | |

| CCA | GAG | AAC | AAC | TAC | CGG | ACG | ACC | CCG | CCC | CAG | CTG | GAC | AGC | GAC | GGG | 864 |
|---|---|---|---|---|---|---|---|---|---|---|---|---|---|---|---|---|
| Pro | Glu | Asn | Asn | Tyr | Arg | Thr | Thr | Pro | Pro | Gln | Leu | Asp | Ser | Asp | Gly | |
| 400 | | | | | 405 | | | | | 410 | | | | | 415 | |

| ACC | TAC | TTC | GTG | TAC | AGC | AAG | CTC | TCG | GTG | GAC | AGG | TCC | CAC | TGG | CAG | 912 |
|---|---|---|---|---|---|---|---|---|---|---|---|---|---|---|---|---|
| Thr | Tyr | Phe | Val | Tyr | Ser | Lys | Leu | Ser | Val | Asp | Arg | Ser | His | Trp | Gln | |
| | | | | 420 | | | | | 425 | | | | | 430 | | |

| AGG | GGA | AAC | ACC | TAC | ACC | TGC | TCG | GTG | TCA | CAC | GAA | GCT | CTG | CAC | AGC | 960 |
|---|---|---|---|---|---|---|---|---|---|---|---|---|---|---|---|---|
| Arg | Gly | Asn | Thr | Tyr | Thr | Cys | Ser | Val | Ser | His | Glu | Ala | Leu | His | Ser | |
| | | | 435 | | | | | 440 | | | | | 445 | | | |

| CAC | CAC | ACA | CAG | AAA | TCC | CTC | ACC | CAG | TCT | CCG | GGT | AAA | TGAGCA | | | 1005 |
|---|---|---|---|---|---|---|---|---|---|---|---|---|---|---|---|---|
| His | His | Thr | Gln | Lys | Ser | Leu | Thr | Gln | Ser | Pro | Gly | Lys | | | | |
| | | 450 | | | | | 455 | | | | | 460 | | | | |

(2) INFORMATION FOR SEQ ID NO:6:

(i) SEQUENCE CHARACTERISTICS:
        (A) LENGTH: 333 amino acids
        (B) TYPE: amino acid
        (D) TOPOLOGY: linear (ii) MOLECULE TYPE: protein (xi) SEQUENCE DESCRIPTION: SEQ ID NO:6:

| | | | | | | | | | | | | | | |
|---|---|---|---|---|---|---|---|---|---|---|---|---|---|---|
| Thr | Thr | Ala | Pro | Ser | Val | Phe | Pro | Leu | Ala | Pro | Ser | Cys | Gly | Thr | Thr |
| 1 | | | | 5 | | | | | 10 | | | | | 15 |
| Ser | Gly | Ala | Thr | Val | Ala | Leu | Ala | Cys | Leu | Val | Leu | Gly | Tyr | Phe | Pro |
| | | | 20 | | | | | 25 | | | | | 30 | | |
| Glu | Pro | Val | Thr | Val | Ser | Trp | Asn | Ser | Gly | Ala | Leu | Thr | Ser | Gly | Val |
| | | | 35 | | | | 40 | | | | | 45 | | | |
| His | Thr | Phe | Pro | Ala | Val | Leu | Gln | Ala | Ser | Gly | Leu | Tyr | Ser | Leu | Ser |
| | 50 | | | | | 55 | | | | | 60 | | | | |
| Ser | Met | Val | Thr | Val | Pro | Ser | Ser | Arg | Trp | Leu | Ser | Asp | Thr | Phe | Thr |
| 65 | | | | | 70 | | | | | 75 | | | | | 80 |
| Cys | Asn | Val | Ala | His | Pro | Ser | Asn | Thr | Lys | Val | Asp | Lys | Thr | Val | |
| | | | | 85 | | | | | 90 | | | | | 95 | |
| Arg | Lys | Thr | Asp | His | Pro | Pro | Gly | Pro | Lys | Pro | Cys | Asp | Cys | Pro | Lys |
| | | | 100 | | | | | 105 | | | | | 110 | | |
| Cys | Pro | Pro | Pro | Glu | Met | Leu | Gly | Gly | Pro | Ser | Ile | Phe | Ile | Phe | Pro |
| | | 115 | | | | | 120 | | | | | 125 | | | |
| Pro | Lys | Pro | Lys | Asp | Thr | Leu | Ser | Ile | Ser | Arg | Thr | Pro | Glu | Val | Thr |
| | 130 | | | | | 135 | | | | | 140 | | | | |
| Cys | Leu | Val | Val | Asp | Leu | Gly | Pro | Asp | Asp | Ser | Asp | Val | Gln | Ile | Thr |
| 145 | | | | | 150 | | | | | 155 | | | | | 160 |
| Trp | Phe | Val | Asp | Asn | Thr | Gln | Val | Tyr | Thr | Ala | Lys | Thr | Ser | Pro | Arg |
| | | | | 165 | | | | | 170 | | | | | 175 | |
| Glu | Glu | Gln | Phe | Asn | Ser | Thr | Tyr | Arg | Val | Val | Ser | Val | Leu | Pro | Ile |
| | | | 180 | | | | | 185 | | | | | 190 | | |
| Leu | His | Gln | Asp | Trp | Leu | Lys | Gly | Lys | Glu | Phe | Lys | Cys | Lys | Val | Asn |
| | | 195 | | | | | 200 | | | | | 205 | | | |
| Ser | Lys | Ser | Leu | Pro | Ser | Pro | Ile | Glu | Arg | Thr | Ile | Ser | Lys | Ala | Lys |
| | 210 | | | | | 215 | | | | | 220 | | | | |
| Gly | Gln | Pro | His | Glu | Pro | Gln | Val | Tyr | Val | Leu | Pro | Pro | Ala | Gln | Glu |
| 225 | | | | | 230 | | | | | 235 | | | | | 240 |

-continued

| Glu | Leu | Ser | Arg | Asn 245 | Lys | Val | Ser | Val 250 | Thr | Cys | Leu | Ile | Lys 255 | Ser | Phe |

| His | Pro | Pro | Asp 260 | Ile | Ala | Val | Glu | Trp 265 | Glu | Ile | Thr | Gly | Gln 270 | Pro | Glu |

| Pro | Glu | Asn 275 | Asn | Tyr | Arg | Thr | Thr 280 | Pro | Pro | Gln | Leu | Asp 285 | Ser | Asp | Gly |

| Thr | Tyr 290 | Phe | Val | Tyr | Ser | Lys 295 | Leu | Ser | Val | Asp | Arg 300 | Ser | His | Trp | Gln |

| Arg 305 | Gly | Asn | Thr | Tyr | Thr 310 | Cys | Ser | Val | Ser | His 315 | Glu | Ala | Leu | His | Ser 320 |

| His | His | Thr | Gln | Lys 325 | Ser | Leu | Thr | Gln | Ser 330 | Pro | Gly | Lys |

(2) INFORMATION FOR SEQ ID NO:7:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..327

(xi) SEQUENCE DESCRIPTION: SEQ ID NO:7:

| AGT | GAT | GCT | CAG | CCA | TCT | GTC | TTT | CTC | TTC | CAA | CCA | TCT | CTG | GAC | GAG | 48 |
| Ser | Asp 335 | Ala | Gln | Pro | Ser | Val 340 | Phe | Leu | Phe | Gln | Pro 345 | Ser | Leu | Asp | Glu | |

| TTA | CAT | ACA | GGA | AGT | GCC | TCT | ATC | GTG | TGC | ATA | TTG | AAT | GAC | TTC | TAC | 96 |
| Leu 350 | His | Thr | Gly | Ser | Ala 355 | Ser | Ile | Val | Cys | Ile 360 | Leu | Asn | Asp | Phe | Tyr 365 | |

| CCC | AAA | GAG | GTC | AAT | GTC | AAG | TGG | AAA | GTG | GAT | GGC | GTA | GTC | CAA | ACA | 144 |
| Pro | Lys | Glu | Val | Asn 370 | Val | Lys | Trp | Lys | Val 375 | Asp | Gly | Val | Val | Gln 380 | Thr | |

| AAG | GCA | TCC | AAG | GAG | AGC | ACC | ACA | GAG | CAG | AAC | AGC | AAG | GAC | AGC | ACC | 192 |
| Lys | Ala | Ser | Lys 385 | Glu | Ser | Thr | Thr | Glu 390 | Gln | Asn | Ser | Lys | Asp 395 | Ser | Thr | |

| TAC | AGC | CTC | AGC | AGC | ACC | CTG | ACG | ATG | TCC | AGG | ACG | GAG | TAC | CAA | AGT | 240 |
| Tyr | Ser | Leu 400 | Ser | Ser | Thr | Leu | Thr 405 | Met | Ser | Arg | Thr | Glu 410 | Tyr | Gln | Ser | |

| CAT | GAA | AAG | TTC | TCC | TGC | GAG | GTC | ACT | CAC | AAG | AGC | CTG | GCC | TCC | ACC | 288 |
| His | Glu 415 | Lys | Phe | Ser | Cys | Glu 420 | Val | Thr | His | Lys | Ser 425 | Leu | Ala | Ser | Thr | |

| CTC | GTC | AAG | AGC | TTC | AAC | AGG | AGC | GAG | TGT | CAG | AGA | GAG | TAGCCTAGCA | | | 337 |
| Leu 430 | Val | Lys | Ser | Phe | Asn 435 | Arg | Ser | Glu | Cys | Gln 440 | Arg | Glu | | | | |

(2) INFORMATION FOR SEQ ID NO:8:

(i) SEQUENCE CHARACTERISTICS:
        (A) LENGTH: 109 amino acids
        (B) TYPE: amino acid
        (D) TOPOLOGY: linear (ii) MOLECULE TYPE: protein (xi) SEQUENCE DESCRIPTION: SEQ ID NO:8:

| Ser 1 | Asp | Ala | Gln | Pro 5 | Ser | Val | Phe | Leu | Phe 10 | Gln | Pro | Ser | Leu | Asp 15 | Glu |

| Leu | His | Thr | Gly | Ser 20 | Ala | Ser | Ile | Val | Cys 25 | Ile | Leu | Asn | Asp | Phe 30 | Tyr |

```
Pro  Lys  Glu  Val  Asn  Val  Lys  Trp  Lys  Val  Asp  Gly  Val  Val  Gln  Thr
          35                       40                      45

Lys  Ala  Ser  Lys  Glu  Ser  Thr  Thr  Glu  Gln  Asn  Ser  Lys  Asp  Ser  Thr
     50                       55                       60

Tyr  Ser  Leu  Ser  Ser  Thr  Leu  Thr  Met  Ser  Arg  Thr  Glu  Tyr  Gln  Ser
65                            70                  75                           80

His  Glu  Lys  Phe  Ser  Cys  Glu  Val  Thr  His  Lys  Ser  Leu  Ala  Ser  Thr
                    85                       90                           95

Leu  Val  Lys  Ser  Phe  Asn  Arg  Ser  Glu  Cys  Gln  Arg  Glu
               100                      105
```

( 2 ) INFORMATION FOR SEQ ID NO:9:

( i ) SEQUENCE CHARACTERISTICS:
        ( A ) LENGTH: 318 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..315

( x i ) SEQUENCE DESCRIPTION: SEQ ID NO:9:

```
CAG  CCC  AAG  TCG  GCC  CCC  TCG  GTC  ACA  CTC  TTC  CCA  CCC  TCC  AGT  GAG      48
Gln  Pro  Lys  Ser  Ala  Pro  Ser  Val  Thr  Leu  Phe  Pro  Pro  Ser  Ser  Glu
110                      115                      120                      125

GAG  CTC  AGC  GCA  AAC  AAG  GCC  ACC  CTG  GTG  TGT  CTC  GTC  AGT  GAC  TTC      96
Glu  Leu  Ser  Ala  Asn  Lys  Ala  Thr  Leu  Val  Cys  Leu  Val  Ser  Asp  Phe
                    130                      135                      140

TAC  CCC  AGC  GGC  TTG  ACG  GTG  GCC  TGG  AAG  GAA  GAT  GGC  ACC  CCC  ATC     144
Tyr  Pro  Ser  Gly  Leu  Thr  Val  Ala  Trp  Lys  Glu  Asp  Gly  Thr  Pro  Ile
                    145                      150                      155

ACC  AAG  GGC  GTG  GAG  ACC  ACC  AAG  CCC  TCC  AGA  CAG  AGC  AAC  AAC  AAG     192
Thr  Lys  Gly  Val  Glu  Thr  Thr  Lys  Pro  Ser  Arg  Gln  Ser  Asn  Asn  Lys
               160                      165                      170

TAC  GCG  GCC  AGC  AGC  TAC  CTG  AGC  CTG  TCA  CCG  AAC  GAG  TGG  AAA  TCT     240
Tyr  Ala  Ala  Ser  Ser  Tyr  Leu  Ser  Leu  Ser  Pro  Asn  Glu  Trp  Lys  Ser
175                      180                      185

CAC  AGC  AGA  TAC  ACC  TGC  CAG  GTC  ACG  CAC  GAG  GGG  AGC  ACT  GTG  GAG     288
His  Ser  Arg  Tyr  Thr  Cys  Gln  Val  Thr  His  Glu  Gly  Ser  Thr  Val  Glu
190                      195                      200                      205

AAG  AGT  GTG  GTC  CCT  GCA  GAG  TGC  CCT  TAG                                    318
Lys  Ser  Val  Val  Pro  Ala  Glu  Cys  Pro
               210
```

( 2 ) INFORMATION FOR SEQ ID NO:10:

( i ) SEQUENCE CHARACTERISTICS:
        ( A ) LENGTH: 105 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Gln  Pro  Lys  Ser  Ala  Pro  Ser  Val  Thr  Leu  Phe  Pro  Pro  Ser  Ser  Glu
1                        5                        10                      15

Glu  Leu  Ser  Ala  Asn  Lys  Ala  Thr  Leu  Val  Cys  Leu  Val  Ser  Asp  Phe
                    20                       25                       30

Tyr  Pro  Ser  Gly  Leu  Thr  Val  Ala  Trp  Lys  Glu  Asp  Gly  Thr  Pro  Ile
```

```
          35                    40                       45
Thr  Lys  Gly  Val  Glu  Thr  Thr  Lys  Pro  Ser  Arg  Gln  Ser  Asn  Asn  Lys
          50                    55                       60

Tyr  Ala  Ala  Ser  Ser  Tyr  Leu  Ser  Leu  Ser  Pro  Asn  Glu  Trp  Lys  Ser
     65                    70                       75                        80

His  Ser  Arg  Tyr  Thr  Cys  Gln  Val  Thr  His  Glu  Gly  Ser  Thr  Val  Glu
                         85                       90                   95

Lys  Ser  Val  Val  Pro  Ala  Glu  Cys  Pro
                100                      105
```

( 2 ) INFORMATION FOR SEQ ID NO:11:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

```
GAAGATCTGG  ATCCACTCAC  CTGCAGAGAC  AGTGA                             35
```

( 2 ) INFORMATION FOR SEQ ID NO:12:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

```
GGAATTCAAG  CTTGCCGCCA  CCATGGTWTY  CTCACCTCAG                        40
```

( 2 ) INFORMATION FOR SEQ ID NO:13:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

```
CTAGATCTGG  ATCCACTTAC  GTTTKATTTC  CARCTT                            36
```

( 2 ) INFORMATION FOR SEQ ID NO:14:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

```
Asp  Val  Gln  His  Ile  Ser  Phe  Gln  Val  Thr  Leu  Lys  Glu  Ser  Gly  Pro
1                        5                        10                       15

Gly  Ile  Leu  Gln  Pro  Ser  Gln  Thr  Leu  Ser  Leu  Thr  Cys  Ser  Phe  Ser
                    20                       25                   30

Gly  Phe  Ser  Leu  Ser  Thr  Ser  Gly  Met  Gly  Val  Ser  Trp  Ile  Arg  Gln
               35                       40                   45
```

| Pro | Ser | Gly | Lys | Gly | Leu | Glu | Trp | Leu | Ala | His | Ile | Tyr | Trp | Asp | Asp |
|     | 50  |     |     |     | 55  |     |     |     |     |     | 60  |     |     |     |     |

| Asp | Lys | Arg | Tyr | Asn | Pro | Ser | Leu | Lys | Ser | Arg | Leu | Thr | Ile | Ser | Lys |
| 65  |     |     |     |     | 70  |     |     |     |     | 75  |     |     |     |     | 80  |

| Asp | Thr | Ser | Arg | Asn | Gln | Val | Phe | Leu | Lys | Ile | Thr | Ser | Val | Asp | Thr |
|     |     |     |     | 85  |     |     |     |     | 90  |     |     |     |     | 95  |     |

| Ala | Asp | Thr | Ala | Thr | Tyr | Tyr | Cys | Ala | Arg | Arg | Glu | Gly | Gly | Arg | Ser |
|     |     |     | 100 |     |     |     |     |     | 105 |     |     |     |     | 110 |     |

| Tyr | Phe | Asp | Tyr | Trp | Gly | Gln | Gly | Thr | Thr |
|     |     | 115 |     |     |     |     | 120 |     |     |

( 2 ) INFORMATION FOR SEQ ID NO:15:

( i ) SEQUENCE CHARACTERISTICS:
        ( A ) LENGTH: 108 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

| Pro | Gly | Ile | Leu | Gln | Pro | Ser | Gln | Thr | Leu | Ser | Leu | Thr | Cys | Ser | Phe |
| 1   |     |     |     | 5   |     |     |     |     | 10  |     |     |     |     | 15  |     |

| Ser | Gly | Phe | Ser | Leu | Ser | Thr | Ser | Gly | Met | Gly | Val | Gly | Trp | Ile | Arg |
|     |     |     | 20  |     |     |     |     | 25  |     |     |     |     | 30  |     |     |

| Gln | Pro | Ser | Gly | Lys | Gly | Leu | Glu | Trp | Leu | Ala | His | Ile | Trp | Trp | Asp |
|     |     |     | 35  |     |     |     |     | 40  |     |     |     |     | 45  |     |     |

| Asp | Asp | Lys | Arg | Tyr | Asn | Pro | Ala | Leu | Lys | Ser | Arg | Leu | Thr | Ile | Ser |
|     | 50  |     |     |     |     | 55  |     |     |     |     | 60  |     |     |     |     |

| Lys | Asp | Thr | Ser | Ser | Asn | Gln | Val | Phe | Leu | Lys | Ile | Ala | Ser | Val | Asp |
| 65  |     |     |     |     | 70  |     |     |     |     | 75  |     |     |     |     | 80  |

| Thr | Ala | Asp | Thr | Ser | Thr | Tyr | Tyr | Cys | Ala | Arg | Asp | Trp | Asp | Tyr | Phe |
|     |     |     |     | 85  |     |     |     |     | 90  |     |     |     |     | 95  |     |

| Asp | Tyr | Trp | Gly | Gln | Gly | Thr | Thr | Leu | Thr | Val | Ser |
|     |     |     | 100 |     |     |     |     | 105 |     |     |     |

( 2 ) INFORMATION FOR SEQ ID NO:16:

( i ) SEQUENCE CHARACTERISTICS:
        ( A ) LENGTH: 114 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

| Gly | Ile | Leu | Gln | Pro | Ser | Gln | Thr | Leu | Ser | Leu | Thr | Cys | Ser | Phe | Ser |
| 1   |     |     |     | 5   |     |     |     |     | 10  |     |     |     |     | 15  |     |

| Gly | Phe | Ser | Leu | Ser | Thr | Ser | Gly | Met | Gly | Val | Gly | Trp | Ile | Arg | Gln |
|     |     |     | 20  |     |     |     |     | 25  |     |     |     |     | 30  |     |     |

| Pro | Ser | Gly | Lys | Gly | Leu | Glu | Trp | Leu | Ala | His | Ile | Trp | Trp | Asp | Asp |
|     |     |     | 35  |     |     |     |     | 40  |     |     |     |     | 45  |     |     |

| Asp | Lys | Arg | Tyr | Asn | Pro | Ala | Leu | Lys | Ser | Arg | Leu | Thr | Ile | Ser | Lys |
|     | 50  |     |     |     |     | 55  |     |     |     |     | 60  |     |     |     |     |

| Asp | Thr | Ser | Ser | Asn | Gln | Val | Ser | Leu | Lys | Ile | Ala | Ser | Val | Asp | Thr |
| 65  |     |     |     |     | 70  |     |     |     |     | 75  |     |     |     |     | 80  |

| Ala | Asp | Thr | Ala | Thr | Tyr | Tyr | Cys | Ala | Arg | Thr | Tyr | Tyr | Tyr | Gly | Ser |
|     |     |     |     | 85  |     |     |     |     | 90  |     |     |     |     | 95  |     |

```
                Ser   His   Trp   Tyr   Phe   Asp   Val   Trp   Gly   Ala   Gly   Thr   Thr   Val   Thr   Val
                                  100                           105                           110

Ser   Ser
```

( 2 ) INFORMATION FOR SEQ ID NO:17:

( i ) SEQUENCE CHARACTERISTICS:
        ( A ) LENGTH: 108 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:17:

```
Pro   Gly   Ile   Leu   Gln   Pro   Ser   Gln   Thr   Leu   Ser   Leu   Thr   Cys   Ser   Phe
 1                       5                           10                          15

Ser   Gly   Phe   Ser   Leu   Ser   Thr   Ser   Gly   Met   Gly   Ser   Trp   Ile   Arg   Gln
                  20                          25                          30

Pro   Ser   Gly   Lys   Gly   Leu   Glu   Trp   Leu   Ala   His   Ile   Tyr   Trp   Asp   Asp
            35                          40                          45

Asp   Lys   Arg   Tyr   Asn   Pro   Ser   Leu   Lys   Ser   Arg   Leu   Thr   Ile   Ser   Lys
      50                          55                          60

Asp   Thr   Ser   Arg   Asn   Gln   Val   Phe   Leu   Lys   Ile   Thr   Ser   Val   Asp   Thr
 65                          70                          75                          80

Ala   Asp   Thr   Ala   Thr   Tyr   Tyr   Cys   Ala   Arg   Ser   Tyr   Gly   Asn   Gly   Asp
                        85                          90                          95

Tyr   Tyr   Ala   Met   Asp   Tyr   Trp   Gly   Gln   Gly   Thr   Ser
                  100                         105
```

( 2 ) INFORMATION FOR SEQ ID NO:18:

( i ) SEQUENCE CHARACTERISTICS:
        ( A ) LENGTH: 127 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:18:

```
Met   Val   Phe   Thr   Pro   Gln   Ile   Leu   Gly   Leu   Met   Leu   Phe   Trp   Ile   Ser
 1                       5                           10                          15

Ala   Ser   Arg   Gly   Asp   Ile   Val   Leu   Thr   Gln   Ser   Pro   Ala   Thr   Leu   Ser
                  20                          25                          30

Val   Thr   Pro   Arg   Asp   Ser   Val   Ser   Leu   Ser   Cys   Arg   Ala   Ser   Gln   Ser
            35                          40                          45

Ile   Ser   Asn   Asn   Leu   His   Trp   Tyr   Gln   Gln   Lys   Ser   His   Glu   Ser   Pro
      50                          55                          60

Arg   Leu   Leu   Ile   Lys   Tyr   Ala   Ser   Gln   Ser   Ile   Ser   Gly   Ile   Pro   Ser
 65                          70                          75                          80

Arg   Phe   Ser   Gly   Ser   Gly   Ser   Gly   Thr   Asp   Phe   Thr   Leu   Ser   Ile   Asn
                        85                          90                          95

Ser   Val   Glu   Thr   Glu   Asp   Phe   Gly   Met   Tyr   Phe   Cys   Gln   Gln   Ser   Asn
                  100                         105                         110

Ser   Trp   Pro   Leu   Thr   Phe   Gly   Ala   Gly   Thr   Lys   Leu   Glu   Leu   Lys
            115                         120                         125
```

( 2 ) INFORMATION FOR SEQ ID NO:19:

( i ) SEQUENCE CHARACTERISTICS:
    ( A ) LENGTH: 100 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:19:

```
Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro His
                85                  90                  95

Thr Phe Gly Ser
            100
```

( 2 ) INFORMATION FOR SEQ ID NO:20:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:20:

```
Asp Ile Val Leu Thr Gln Ser Pro Ala Thr Leu Ser Val Thr Pro Gly
1               5                   10                  15

Asn Ser Val Ser Leu Ser Cys Arg Ala Ser Gln Ser Ile Gly Asn Asn
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
        50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Tyr
                85                  90                  95

Thr Phe Gly Gly Gly Thr Lys Leu Glu Ile Lys
            100                 105
```

( 2 ) INFORMATION FOR SEQ ID NO:21:

( i ) SEQUENCE CHARACTERISTICS:
        ( A ) LENGTH: 103 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:21:

```
Ile Val Leu Thr Gln Ser Pro Ala Thr Leu Ser Val Thr Pro Gly Asp
1               5                   10                  15
```

```
Ser  Val  Leu  Ser  Cys  Arg  Ala  Ser  Gln  Ser  Ile  Ser  Asn  Asn  Leu  His
               20                       25                      30

Trp  Tyr  Gln  Gln  Lys  Ser  His  Glu  Ser  Pro  Arg  Leu  Leu  Ile  Asn  Tyr
          35                       40                      45

Ala  Ser  Gln  Ser  Ile  Ser  Ile  Pro  Ser  Arg  Phe  Ser  Gly  Ser  Gly  Ser
     50                       55                      60

Gly  Thr  Asp  Phe  Thr  Leu  Ile  Ile  Asn  Asn  Val  Glu  Thr  Glu  Asp  Phe
65                       70                      75                           80

Gly  Met  Tyr  Phe  Cys  Gln  Gln  Ser  Asn  Ser  Trp  Pro  Leu  Thr  Phe  Ala
               85                       90                           95

Ala  Gly  Thr  Lys  Leu  Glu  Leu
               100
```

ANTI-FELINE HERPES VIRUS-1 RECOMBINANT ANTIBODY AND GENE FRAGMENT CODING FOR SAID ANTIBODY

CROSS-REFERENCE TO RELATED APPLICATIONS

This is a 371 national stage application of PCT/JP93/01724, filed Nov. 25, 1993.

TECHNICAL FIELD

The present invention relates to a novel feline monoclonal antibody usable for diagnosis, treatment and prevention of feline herpes virus-1 (FHV-1) infection. More particularly, it relates to a felinized anti-FHV-1 recombinant antibody wherein a constant region of a mouse-type anti-FHV-1 neutralizing monoclonal antibody is replaced with a feline antibody constant region, and a gene fragment encoding said antibody.

BACKGROUND ART

A cat is such an animal that has been loved by humans as a pet from ancient times and, in modern times, called as Companion species, is becoming a member of a human society. On the other hand, a cat has hitherto greatly contributed to humans as an experimental animal in various fields such as medicine, pharmaceutics, animal husbandry veterinary and psychology, and in recent years, the contribution of a cat has further increased to be used as an SPF Cat in an effectiveness assay or safety test for drugs. In any case, as a matter of course, more reliable knowledge on feline diseases, especially on infectious diseases, is increasingly needed and the establishment of a method for diagnosis, treatment and prevention of these diseases is required.

Many viral diseases of cats have been known. Among them, an upper tracheal disease caused by FHV-1 is acute and shows a high lethality. For both diseases, there is no specific treating drug and only a symptomatic treatment for preventing a secondary infection by the use of antibiotics, sulfonamide drugs, etc., and hence, there remains a problem in a conventional method for treatment.

Hitherto, a hiperimmune serum or a serum-derived immunoglobulin have been used as a medicament for treatment of viral diseases and have shown satisfactory results. Nowadays, however, feline serum materials are hardly available due to promotion of Be-Kind-to-Animals thought, and hence, we are in a situation that this treating method cannot be used in spite of desire to use this method. Accordingly, in place of the conventional hiperimmune serum, a monoclonal antibody capable of neutralizing FHV-1 will possibly greatly contribute to the treatment of FHV-1 infection.

PRIOR ART

There have been established several neutralizing monoclonal antibodies against FHV-1. However, all the monoclonal antibodies established hitherto are antibodies derived from a mouse hybridoma. When these antibodies are administered to a cat as a medicament, since they are a heterogeneous protein, they will show weaker binding capacity to complement or immunocompetent cells having an Fc receptor present in blood than that of homo species (cat) and appear to hardly induce cell damage by "antibody+complement" or antibody-dependent cellular cytotoxicity, cell-mediated cell damage. It is known that, in addition to the action by an antibody alone, these two immune reactions are also important for prevention of FHV-1 infection and for neutralization of virus (Horimoto T. et al., Jpn. J. Vet. Sci. 51, p1025, 1989). Therefore, it is possible that the conventional mouse antibodies cannot exhibit efficacious results in treatment.

Furthermore, it is also possible that the mouse antibodies recognized as a heterogeneous protein cause a side effect such as anaphylaxic shock or serum disease or show a shortened half-life, resulting in a decreased efficacy in treatment. Accordingly, when administered, the conventional mouse monoclonal antibodies have never been satisfactory but a felinized monoclonal antibody should have been used.

DISCLOSURE OF THE INVENTION

Under the circumstances, the present inventors have established a mouse monoclonal antibody, JH2, which neutralizes FHV-1 viral strain, have identified a nucleotide sequence of a gene encoding a variable region (V region) of said antibody, and have found a specific amino acid sequence in V region of said antibody which is deeply involved in the neutralization of FHV-1. Then, in order to felinize this mouse type monoclonal antibody, the present inventors have constructed a vector expressing an anti-FHV-1 chimeric antibody having an FHV-1 neutralizing activity by ligating the antibody V region gene coding for the anti-FHV-1 neutralizing antibody with a gene fragment coding for a constant region of feline antibody which the present inventors have previously found, have expressed said vector, and have successfully obtained the anti-FHV-1 chimeric antibody. That is, an object of the present invention is to provide an anti-FHV-1 felinized chimeric antibody which has hitherto never been reported and is prepared by utilizing a genetic engineering technique by replacing the constant region of the mouse-type antibody with a constant region of a feline antibody, and to provide a gene fragment coding for said antibody useful for production of the same. Thus, now it becomes possible to apply an anti-FHV-1 antibody as diagnostic, treating and preventing agents which is effective against FHV-1 infection without side effects.

BRIEF EXPLANATION OF DRAWINGS

FIG. 2 shows a base sequence (SEQ ID NO:1) of a VH gene obtained in Example (3) and an amino acid sequence (SEQ ID NO:2) encoded by said gene.

FIG. 3 shows a base sequence (SEQ ID NO:3) of a Vκ gene obtained in Example (4) and an amino acid sequence (SEQ ID NO:4) encoded by said gene.

FIG. 4 shows results of homologous comparison of the VH region between JH2 (SEQ ID NO:2) and other antibodies (SEQ ID NOS:14–17) at an amino acid level.

FIG. 5 shows results of homologous comparison of the Vκ region between JH2 (SEQ ID NO:4) and other antibodies (SEQ ID NOS:18–21) at an amino acid level.

BEST MODE FOR PRACTICING THE INVENTION

Figure 1:
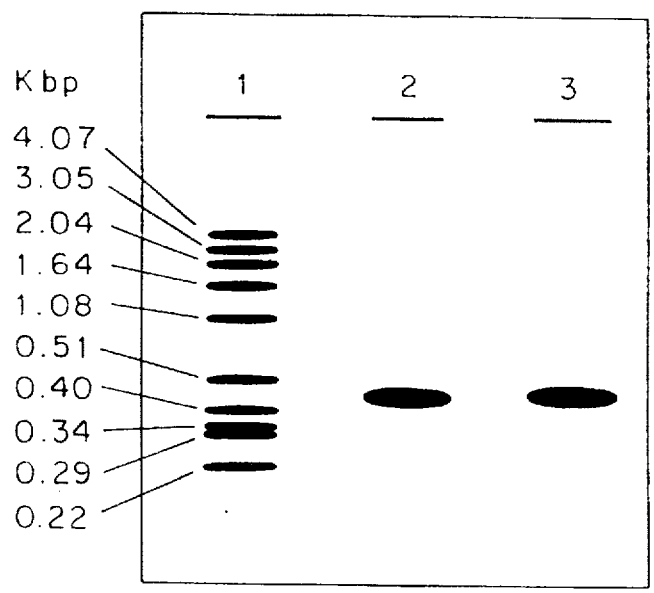
FIG. 1 illustrates results of agarose gel electrophoresis of VH, Vκ genes of the anti-FHV-1 antibody JH2 amplified by PCR.

First, the present inventors have conducted a cell fusion between a lymphocyte of mice immunized with FHV-1-K1 viral particles and a mouse myeloma cell in accordance with the conventional manner to prepare a hybridoma. As a result of cloning with an index of viral neutralizing activity in culture supernatant of hybridomas, the present inventors have successfully established an antibody-producing cell, JH2, which produces a monoclonal antibody being quite excellent in FHV-1 neutralizing activity.

It is generally known that a specificity of an antibody against an antigen is based on amino acids in a variable (V) region of an antibody. Thus, the present inventors have studied what amino acids constitute V region of JH2. The amino acid sequence was determined by cloning a gene coding for V region of said antibody and studying a nucleotide sequence thereof.

As a result, V region was found to have the amino acid sequence as shown in FIGS. 3 and 4. Generally, there exist about 200 VH, about several 10s D, and 4 JH genes in an H chain gene region of an antibody. On the other hand, there are about 200 Vκ, and 4 Jκ genes in an L(κ) chain gene region. It is known that, with differentiation of B cells, each one gene is selected from these V(D)J gene fragments and rearranged to form a gene coding for an amino acid of a whole variable region. Addition of N sequence and a Somatic Mutation give a great number of varieties of an antibody variable region. The variable region gene of JH2 of the present invention is a unique one selected among such varieties. CDR shown in Figures is an important region for binding with an antigen. Also in case of JH2, it appears that the amino acid of these six CDR regions binds with FHV to induce a neutralizing reaction. Especially, "Asp Gly Ala Trp Phe Pro Phe" (corresponding to amino acid residues 126 to 132 of SEQ ID NO:2) in H chain CDR3 was found to be an unique amino acid sequence by a homologous comparison with variable regions of another antibodies.

Accordingly, the amino acids of H chain CDR3 as well as another CDR regions of H and L chains are considered to be closely related to binding and neutralizing reactions with FHV-1. This has been firstly revealed by isolating the variable region gene of JH2 antibody. Determination of a nucleotide sequence and an amino acid sequence of JH2 antibody further enables, based on these sequences, enhancement of an antigen-binding activity and felinization of V region itself. An antibody or a peptide having such amino acid sequence is conjectured to be usable for treatment, diagnosis and prevention of FHV-1 infection.

That is, the gene fragment coding for V region of the antibody having a neutralizing activity against FHV-1 as provided according to the present invention is a gene fragment having the following characteristics.

A gene fragment coding for VH or a part thereof of the antibody which specifically reacts with feline herpes virus-1 (FHV-1) is a gene fragment of VH of the antibody wherein the nucleotide sequence coding for CDR3 of said antibody is a nucleotide sequence coding for the following amino acid sequence:

Asp Gly Ala Trp Phe Pro Phe (amino acid residues 126 to 132 of SEQ ID NO:2).

A preferable gene fragment of VH having a nucleotide sequence coding for such sequence includes a gene fragment wherein nucleotide sequences coding for CDRs 1 to 3 of said antibody are nucleotide sequences each coding for the following amino acid sequences:

CDR1: LeuSerThrSerGlyMetGlyAlaGly (amino acids 48 to 56 of SEQ ID NO:2)

CDR2: HisIleTrpTrpAspAspValLysArg-TyrAsnProAlaLeuLysSer (amino acids 71 to 86 of SEQ ID NO:2)

CDR3: SerGlnIleTyrPheAspTyrAspGly-AlaTrpPheProPhe (amino acids 119 to 132 of SEQ ID NO:2)

Furthermore, by way of example, a preferable sequence of the above VH gene fragment includes a nucleotide sequence coding for the amino acid sequence as described in Sequence Listing: SEQ ID NO:2. A specific nucleotide sequence includes, for example, the nucleotide sequence corresponding to nucleotides 21 to 449 of SEQ ID NO:1.

On the other hand, a gene fragment coding for VL or a part thereof of the antibody which specifically reacts with feline herpes virus-1 (FHV-1) includes a gene fragment wherein nucleotide sequences coding for CDRs 1 to 3 of said antibody are nucleotide sequences each coding for the following amino acid sequences:

CDR1: ArgAlaSerGlnSerIleSerAsnAsnLeuHis (amino acids 44 to 54 of SEQ ID NO:4)

CDR2: AlaSerGlnSerIleSerGly (amino acids 71 to 77 of SEQ ID NO:4)

CDR3: GlnGlnSerAsnSerTrpProHisThr (amino acids 109 to 117 of SEQ ID NO:4)

Furthermore, by way of example, a preferable sequence of the above VL gene fragment includes a nucleotide sequence coding for the amino acid sequence as described in Sequence Listing: SEQ ID NO:4. A specific nucleotide sequence includes, for example, the nucleotide sequence corresponding to nucleotides 23 to 403 of SEQ ID NO:3.

In the meanwhile, it appears to be difficult to administer directly to cats the mouse-type antibody JH2 for treatment of FHV-1 infection in view of reduction of efficacy, side effects, shortened half-life, etc. This is because the antibody itself is a protein heterogeneous to cats derived from mice, and hence, one can foresee that said antibody cannot possibly bind to a complement or immunocompetent cells having Fc receptor of cats, and as a result, ADCC or CDC is hardly inducible. As mentioned above, considering that these activities greatly contribute to the viral neutralization in FHV infection, the antibody needs to have an Fc region derived from cats.

Furthermore, if the antibody exhibits immunogenicity as a heterogenous protein within the living body, it is possibly cleared away quickly from the living body to shorten the half-life or it may provoke side effects such as a serum disease. It is said that the immunogenicity of an antibody molecule is localized in the Fc region. In this sense, the Fc region preferably has an amino acid sequence of an antibody molecule derived from cats as a homogenous protein.

Now, the present inventors have successfully prepared a felinized JH2 by replacing the antibody constant region of JH2 with that derived from cats utilizing a genetic engineering technique.

Such felinized antibody, i.e. anti-FHV-1 chimeric antibody, can be prepared by ligating the feline antibody constant region gene; CH gene and CL gene to the downstream (3' site) of the above-mentioned gene coding for VH of anti-FHV-1 antibody and the VL gene provided by the present invention to construct a structural gene of antibody H chain and L chain coding for said felinized antibody, i.e. felinized chimeric antibody, and expressing said structural gene in a suitable animal cell, etc.

The gene coding for such feline antibody constant region has previously been found by the present inventors (Japanese Patent First Publication No. 3-123488, Japanese Patent First Publication No. 3-201986 and Japanese Patent First Publication No. 3-72873). A nucleotide sequence of the gene coding for such feline antibody constant region includes, as a gene fragment coding for CH, that of a gene fragment coding for the amino acid sequence as described in Sequence Listing: SEQ ID NO:6. A specific nucleotide sequence of said gene includes the nucleotide sequence as described in Sequence Listing: SEQ ID NO:5. As a gene coding for Cκ, a nucleotide sequence of said gene includes that of a gene fragment coding for the amino acid sequence as described in Sequence Listing: SEQ ID NO:8. A specific nucleotide sequence of said gene includes the nucleotide sequence as described in Sequence Listing: SEQ ID NO:7. As a gene coding for Cλ, a nucleotide sequence of said gene includes that of a gene fragment coding for the amino acid sequence as described in Sequence Listing: SEQ ID NO:10. A specific nucleotide sequence of said gene includes the nucleotide sequence as described in Sequence Listing: SEQ ID NO:9.

The gene fragment coding for V region of the antibody having a neutralizing activity against FHV-1 of the present invention, in addition to the production of the chimeric antibody comprising the mouse-derived V region and the cat-derived C region as mentioned above, can also be used for preparing a reshaped antibody in which a frame (FR) region of V region is also replaced with that derived from an antibody of animals other than mice (in case of the present invention, derived from a feline antibody). There has not yet been totally reported an amino acid sequence of a general V region FR region of a feline antibody. However, a part of such sequence has already been reported (KEHO J. M. et al., Proc. N.A.S. 69, p2052, 1972). Based on these and the amino acid sequence of the constant region of feline antibody which the present inventors have previously found etc., it will be possible to prepare a suitable primer, to clone a gene coding for a feline antibody V region and to determine an amino acid sequence of said FR region. A reshaped antibody can be prepared basically in accordance with the known technique (for example, Japanese Patent First Publication No. 62-296890). The gene fragment of the present invention used in this case is referred to, as a part of a gene coding for VH chain and VL chain, a gene fragment containing at least a nucleotide sequence coding for the following amino acid sequence:

Asp Gly Ala Trp Phe Pro Phe (amino acid residues 126 to 132 of SEQ ID NO:2).

Preferably, nucleic acids coding for CDRs in V region of said reshaped antibody are those coding for the following amino acid sequences for VH chain and VL chain, respectively:

VH chain:
CDR1: LeuSerThrSerGlyMetGlyAlaGly (amino acids 48 to 56 of SEQ ID NO:2)
CDR2: HisIleTrpTrpAspAspValLysArg-TyrAsnProAlaLeuLysSer (amino acids 71 to 86 of SEQ ID NO:2)
CDR3: SerGlnIleTyrPheAspTyrAspGly-AlaTrpPheProPhe (amino acids 119 to 132 of SEQ ID NO:2)

VL chain:
CDR1: ArgAlaSerGlnSerIleSerAsnAsnLeuHis (amino acids 44 to 54 of SEQ ID NO:4)
CDR2: AlaSerGlnSerIleSerGly (amino acids 71 to 77 of SEQ ID NO:4)
CDR3: GlnGlnSerAsnSerTrpProHisThr (amino acids 109 to 117 of SEQ ID NO:4)

In addition, the present inventors have further found previously that, in preparing the reshaped antibody as mentioned above, an antibody having an excellent specificity of the original mouse monoclonal antibody can sometimes be prepared by replacing a portion of FR region of V region adjacent to CDRs with that derived from mice in addition to replacement of CDRs in V region with those derived from mice rather than replacement of CDRs alone in V region with those derived from mice in accordance with the conventional technique. That is, by replacing a portion of FR region of V region as well with that derived from mice by reference to the amino acid sequence described in FIG. 2 for VH chain and the amino acid sequence described in FIG. 3 for VL chain, a reshaped antibody can possibly be prepared which is more excellent than the reshaped antibody in which only CDRs are replaced with those derived from mice.

As mentioned above, the structural gene coding for the felinized anti-FHV-1 recombinant antibody (so called chimeric antibody) is prepared by constructing a V region structural gene for a chimeric antibody or a reshaped antibody by the use of the gene coding for the variable region of the anti-FHV-1 antibody of the present invention and ligating this structural gene with the gene coding for the constant region of feline antibody which the present inventors have previously found. The recombinant antibody of the present invention obtained by ligating this structural gene to the downstream of a suitable promotor gene and expressing the resultant in an animal cell, etc. in accordance with the known technique retained an excellent neutralizing activity like the mouse-type antibody JH2. When administered to FHV-infected cats, the recombinant antibody of the present invention alleviated the disease state without any significant side effect. E. A. Emini et al. have studied a preventive effect of a monoclonal antibody against HIV infection in chimpanzee. As a result, it was found that a humanized chimeric antibody could prevent HIV infection (E. A. Emini et al., Nature, 355, p728, 1992) but the original mouse-type antibody could not (E. A. Emini et al., J. Virol., 64, p3674, 1990). It appears that this is because the latter could not induce Fc region-dependent ADCC or CDC activities and showed a shortened half-life.

As for the effectiveness of FH2 antibody in FHV-infected cats found by the present inventors this time, it appears that the mouse-type antibody has a weak effect but the effect can be exerted only by the felinized antibody like the above-mentioned previous case.

From the above-mentioned point of view, the anti-FHV-1 chimeric antibody FH2 of the present invention can be a substantial medicament for treatment and prevention of FHV-1 infection.

The present invention is explained in more detail hereinbelow by means of Example.

EXAMPLE (1) Production of hybridoma producing anti-FHV-1 neutralizing monoclonal antibody A culture supernatant of FL cells (feline lung cells) infected with FHV-1 was precipitated with ammonium sulfate. After dialysis, the precipitate was resuspended in a phosphate buffer and administered peritoneally to BALB/c mouse for immunization together with Freund's complete adjuvant. After two weeks, mouse lymphocytes and mouse myeloma cells (P3U1) were cell-fused by the polyethylene glycol method to prepare hybridomas. Cloning was conducted by an index of a viral neutralizing activity of culture supernatant of hybridomas and thereby four kinds of FHV-1 neutralizing monoclonal antibody producing cells were established. The following Table 1 shows a minimum effective concentration of each monoclonal antibody necessary for neutralizing 10 $TCID_{50}$ of FHV-1. Among these monoclonal antibodies, JH2 antibody most strongly neutralized FHV-1-K1 strain.

TABLE 1

| Name of antibody | Class | Minimum effective concentration for neutralization (μg/ml) |
|---|---|---|
| JH2 | γ1, κ | 0.39 |
| JH3 | γ1, κ | 6.3 |
| JH4 | γ1, κ | 100 |
| JH7 | γ2a, κ | 6.3 |

(2) Isolation of variable region gene of anti-FHV-1 antibody (JH2)

Whole RNAs were extracted from 1 to $0.5 \times 10^7$ cells (hybridomas) and mRNAs were purified with Oligo dT column (manufactured by Stratagene, Poly(A) Quick mRNA Purification Kit). A single-stranded cDNA was synthesized with reverse transcriptase (Takara; all reagents used for genetic engineering were those manufactured by Takara unless otherwise mentioned).

Oligonucleotides having a base sequence at the leader region (MHL34, MKL104) as a 5' primer and those having a base sequence at the J region (MHJ3, MKJ124) as a 3' primer were synthesized. The base sequence of these primers are shown hereinbelow.

Primer for amplification of VH chain
  MHL341: TCTAGAAGCTTGCCGCCACCATGGGCA-GACTTACATTCTCATT (nucleotides 1 to 43 of SEQ ID NO:1)
  MHJ3 : GAAGATCTGGATCCACTCACCTGCA-GAGACAGTGA (SEQ ID NO:11)
Primer for amplification of VK chain
  MKL104: GGAATTCAAGCTTGCCGCCACCATGGT(T/A)T(C/T)CTCACCTCAG (SEQ ID NO:12)
  MKJ124: CTAGATCTGGATCCACTTACGTTT(T/G)ATTTCCA(A/G)CTT (SEQ ID NO:13)

To 20 ng of cDNA were added each 50 pmol of primers. PCR (Polymerase Chain Reaction) was conducted for 30 cycles, each cycle comprising 94° C. for 1 minute, 55° C. for 1 minute and 72° C. for 1 minute, to amplify the variable region gene (VH, Vκ) flanked by both primers. FIG. 1 shows an agarose electro-phoresis pattern of the amplified gene fragments. A size of VH (H chain) and Vκ (L chain) genes were about 400 bp and about 400 bp, respectively, and virtually corresponded to the bands as expected.

(3) Determination of base sequence

A base sequence of each gene fragment amplified in 1 was determined by the dideoxy method. Each of VH and Vκ gene fragments was cloned into pUC18 and a base sequence thereof was determined by the dideoxy method (manufactured by USB, Sequenase ver. 2).

FIG. 2 shows a base sequence of VH gene of JH2 antibody and an amino acid sequence coded by said gene. This gene took an open reading frame (ORF) and preserved Cys for forming a domain structure, and hence, was found to be suitable for expression. It was also found that rearrangement occurred at JH3. Then, a homology reference was conducted for the amino acid sequence coded by this gene. Using GENETYX-CD (Software) as a reference software, a data base of Gene Bank was referenced. As a result, antibodies 1 to 5 belonging to VHIII/J606 family were found to have highly homologous VH (FIG. 4). In FIG. 4, the mark (*) shows an amino acid homologous to that of other VHs and the region other than this mark represents an amino acid sequence found only in JH2. Especially, the underlined portion represents a novel amino acid sequence which has hitherto never been reported and is characteristic region of JH2 antibody.

FIG. 3 shows a base sequence of Vκ gene of JH2 antibody and an amino acid sequence coded by said gene. Like in case of H chain, this gene took ORF and preserved Cys for forming a domain structure, and hence, was found to be suitable for expression. It was also found that rearrangement occurred at Jκ1. FIG. 5 shows a result of a homology reference. Vκ of JH2 also showed homology with other Vκ.

That is, it appeared that the underlined portion in VH chain is specific for JH2 antibody and is an important amino acid sequence responsible for an antigen binding activity.

(4) Preparation of anti-FHV-1 chimeric antibody genes

Figure 6:
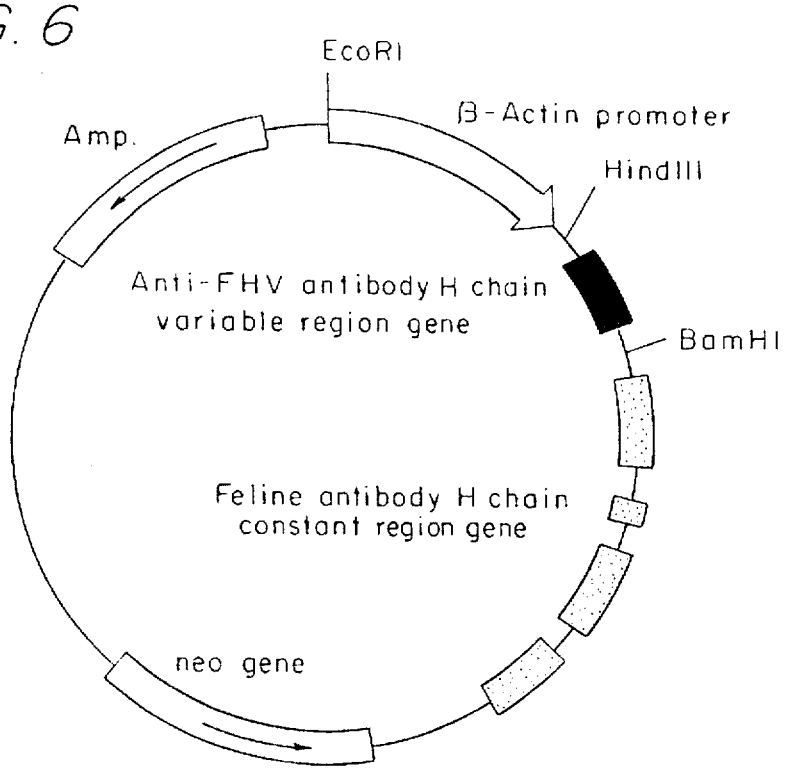
FIG. 6 shows a restriction enzyme map of a vector expressing an H chain of anti-FHV-1 chimeric antibody.
Figure 7:
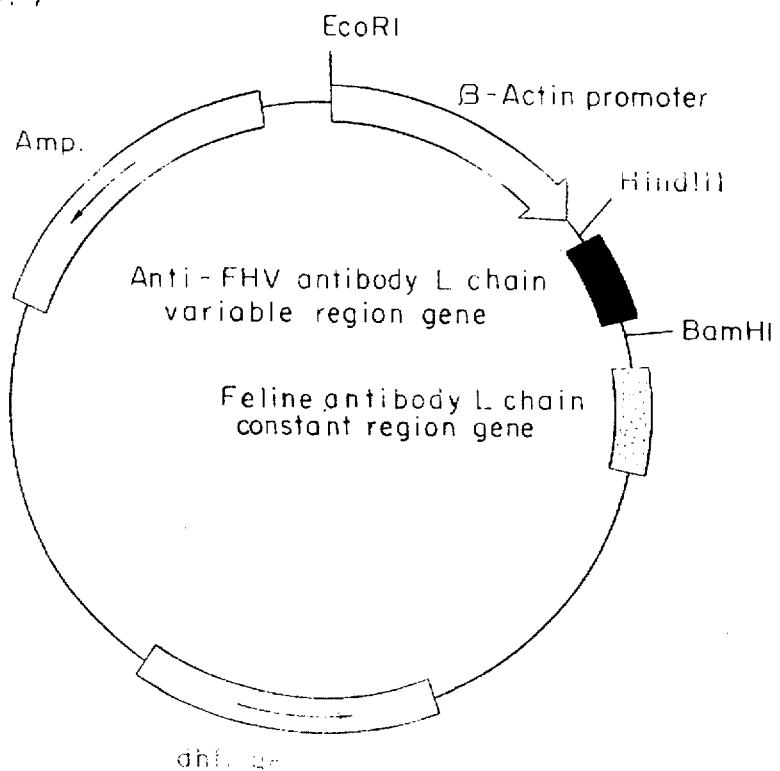
FIG. 7 shows a restriction enzyme map of a vector expressing an L chain of anti-FHV-1 chimeric antibody.

The variable region genes amplified by PCR were ligated to the gene coding for γ chain constant region of feline antibody CB25γ (Japanese Patent First Publication No. 3-201986) or to the gene coding for κ chain constant region of feline antibody CEK (Japanese Patent First Publication No. 3-123488). There were used the chicken β-actin promoter (Japanese Patent Application No. 1-309785) as an expression promoter and neo (Southern P. J. J. Mol. Appl. Genet., 1, 327, 1982) or dhfr gene (Stark, G. R. and Wahl, G. M., Annu. Rev. Biochem., 53, p447, 1984) as a selection marker. FIG. 6 and FIG. 7 show restriction enzyme maps of the chimeric antibody H chain and L chain expression vectors prepared, respectively.

(5) Preparation of stable tranformant

Each 10 μg of the gene coding for the chimeric antibody H chain and L(κ) chain as shown in FIG. 6 and FIG. 7 were digested with PvuI and $2 \times 10^6$ mouse myeloma cells P3-X63-Ag8-6.5.3 (ATCC CRL1580) were co-transfected with the digested products by using lipofectin (manufactured by BRL). The transfected cells were cultured in 5% FCS/RPMI1640 selection medium containing $0.25 \times 10^{-7}$M methotrexate (MTX) to select drug-resistant strains (transformant).

Chimeric antibody producing cells were cloned by a limiting dilution method with an index of feline IgG expressed in culture supernatant to establish an expression cell, FH2. The properties of this cell were analyzed as follows.

(6) Reaction with anti-feline antibody

Figure 8:
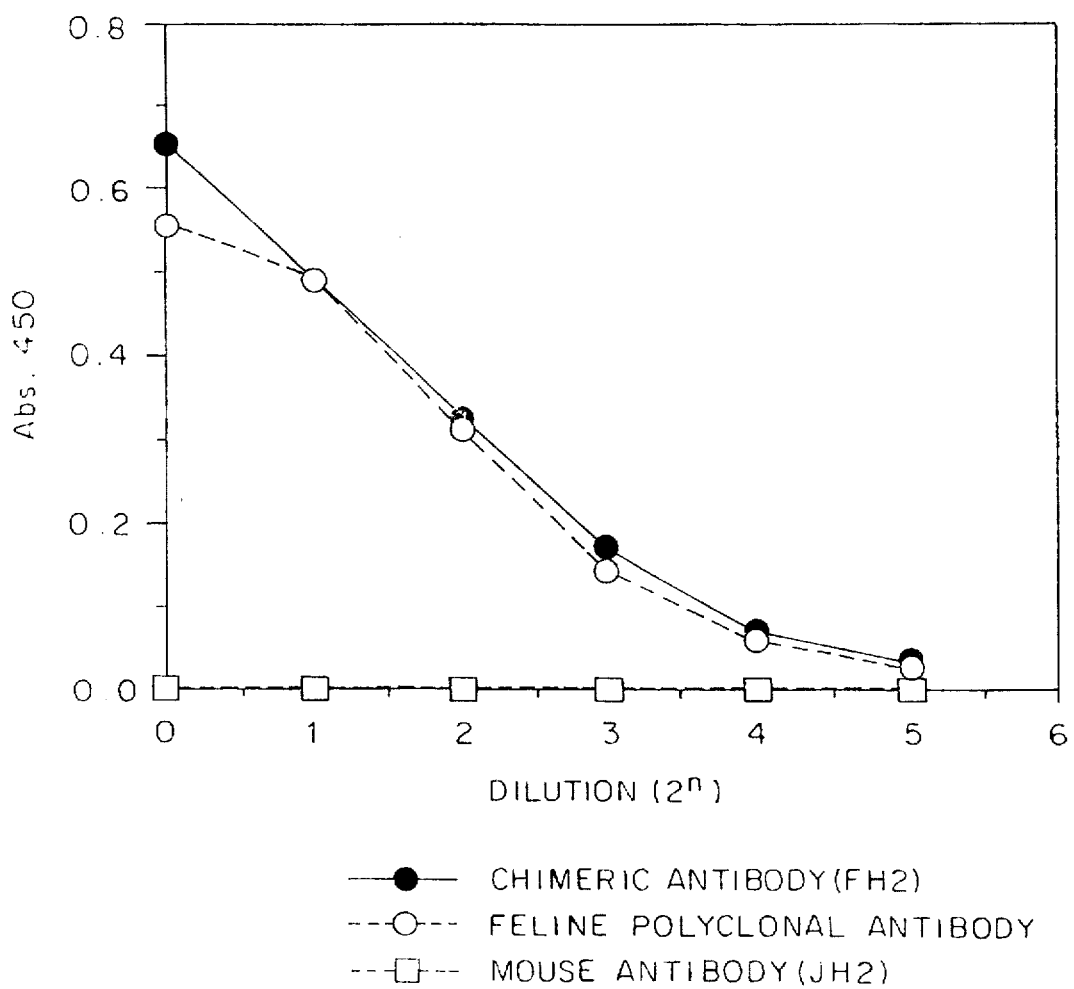
FIG. 8 shows a reactivity of the chimeric antibody of the present invention with an anti-feline antibody.

Culture supernatants of FH2 (chimeric antibody expressing cell) and of JH2 (mouse monoclonal antibody expressing cell) were added to a microtiter plate immobilized with an anti-feline antibody (E.Y.LABS.INC) and the reaction was conducted at room temperature for 1 hour. After washing the plate, HRP-anti-feline antibody (E.Y.LABS.INC) was reacted at room temperature for 1 hour. After washing the plate again, color was developed with TMBZ and an absorbance at 450 nm was measured to analyze the reactivity with the anti-feline antibody (FIG. 8).

The culture supernatant of FH2 reacted with the anti-feline antibody in a concentration-dependent manner whereas the culture supernatant of JH2 which expresses the mouse antibody did not react with the anti-feline antibody. This revealed that the chimeric antibody expressed by FH2 cells is a feline antibody.

(7) Identification of chimeric antibody by SDS-PAGE

The chimeric antibody was purified from the culture supernatant with Protein A (manufactured by Bio Rad, MAPS-II). The purified chimeric antibody was subjected to 12.5% SDS-PAGE and compared with a feline IgG sample (polyclonal antibody). A molecular weight of the purified antibody was determined with a prestained marker manufactured by Bio Rad.

Figure 9:
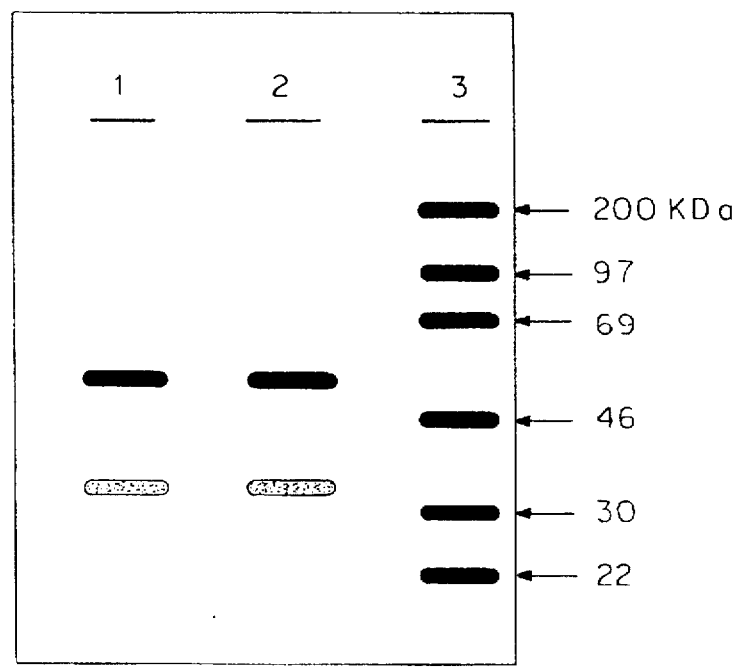
FIG. 9 is an illustration showing results of SDS-PAGE of the chimeric antibody of the present invention.

As shown in FIG. 9, the chimeric antibody detected bands at $5 \times 10^4$ for H chain and at $2.5 \times 10^4$ for L chain under reduced conditions and a band at around $1.5 \times 10^5$ under non-reduced conditions. This revealed that H and L chains form a dimer of H2L2 which has the same form as that of IgG present in the cat body.

(8) Reaction with FHV-1 viral particle

Figure 10:
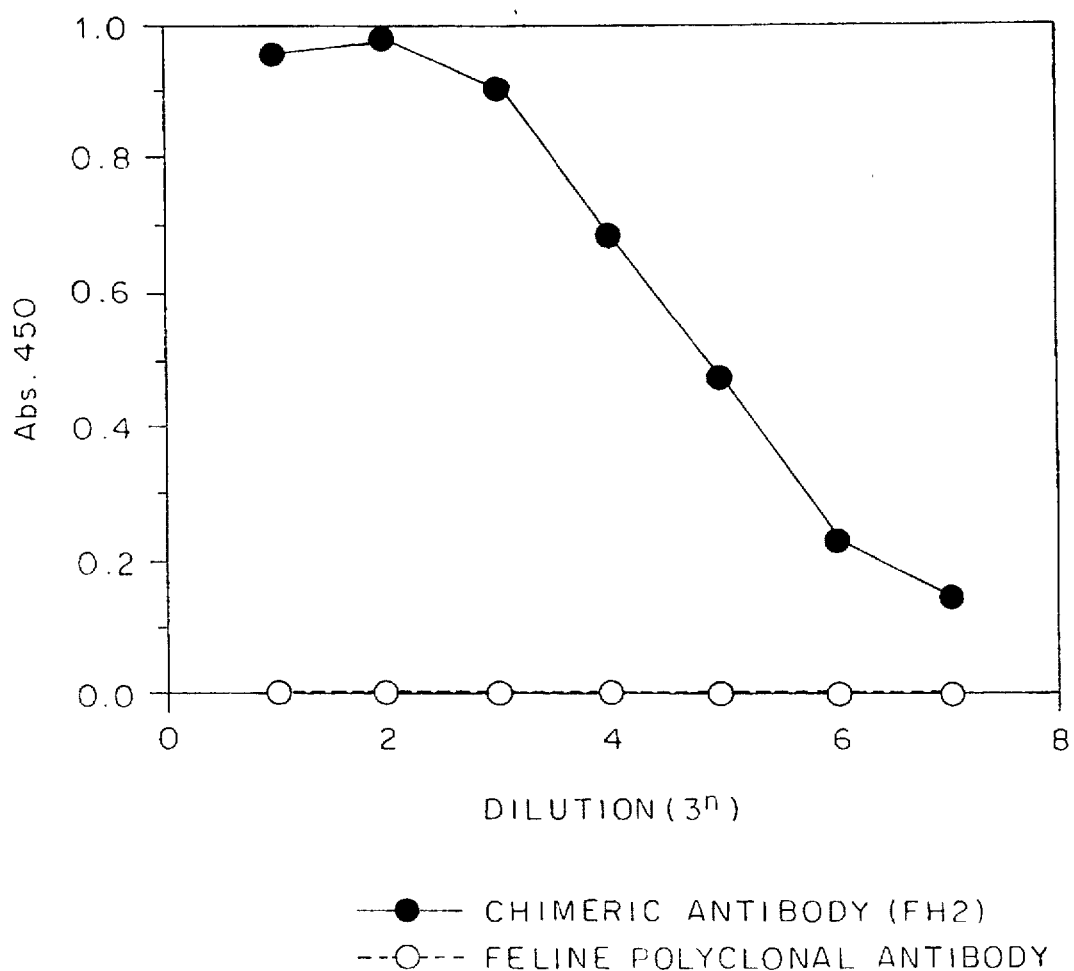
FIG. 10 shows a binding of the chimeric antibody of the present invention to FHV-1.

Then, an antigen binding activity of the chimeric antibody was studied. The culture supernatant (from FH2 and JH2) was added to a microtiter plate immobilized with FHV-1-K1 (crude product by the ammonium sulfate precipitation). After washing the plate, it was reacted with either HRP-anti-feline antibody or HRP-anti-mouse antibody. Color was developed with TMBZ and the reactivity with FHV-1 viral particle was studied. Like the mouse antibody JH2, FH2 antibody specifically reacted with FHV-1-K1. However, the recombinant chimeric antibodies specific for another viruses (antibodies having the same feline constant region and different mouse variable regions) did not reacted (FIG. 10).

(9) Neutralization test against FHV-1 virus

Then, the neutralization activity against FHV-1 of the chimeric antibody was studied. The culture supernatant (from FH2 and JH2) was reacted with 100 $TCID_{50}$ of FHV-1 virus at 4° C. for 6 hours. Thereto were added $0.25 \times 10^5$ CRFK cells and cultured at 37° C. for 2 days. CPE (Cell Rounding) was observed and a minimum effective concentration for neutralization was determined.

The results are summarized in the following Table 2. As a result, it was confirmed that FH2 antibody neutralizes FHV-1 at 1.95 μg/ml.

TABLE 2

| Antibody | Minimum Effective Concentration for Neutralization (μg/ml) |
|---|---|
| Chimeric antibody (FH2) | 1.95 |
| Mouse antibody (JH2) | 1.25 |

(10) Effectiveness and safety of FH2 in cats compulsorily infected with FHV

Figure 11:
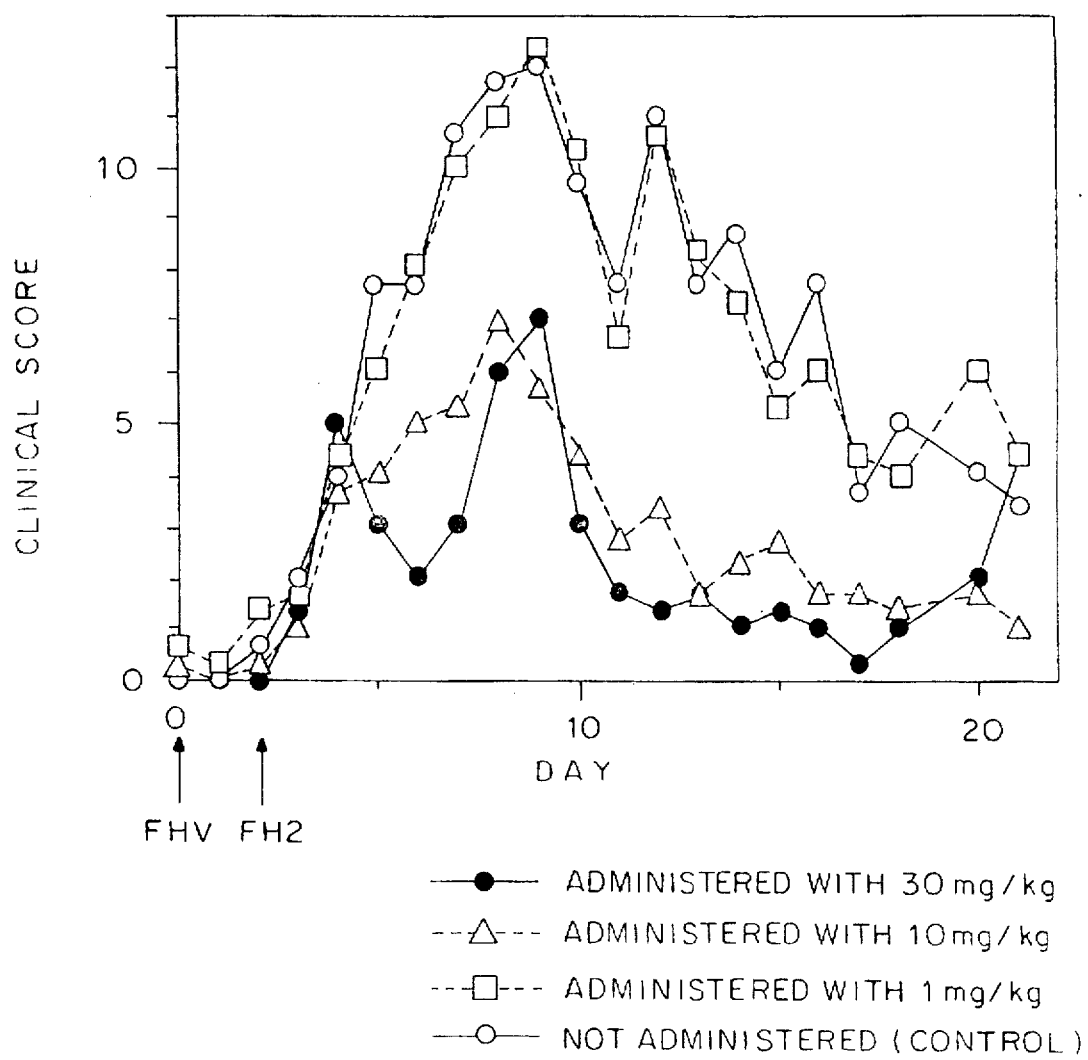
FIG. 11 shows effectiveness of the chimeric antibody of the present invention for cats compulsorily infected with FHV-1 K1 strain.
Figure 12:
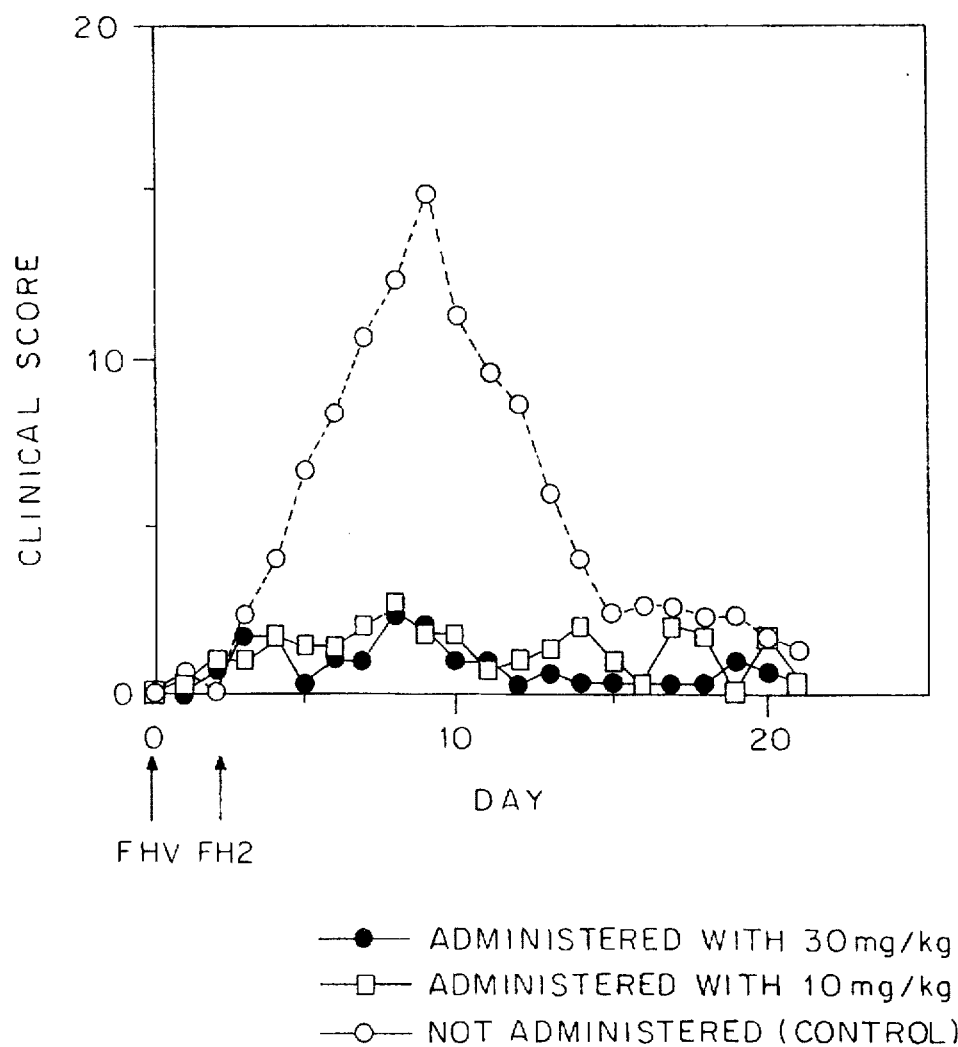
FIG. 12 shows effectiveness of the chimeric antibody of the present invention for SPF cats compulsorily infected with FHV-1 K1 strain.

Cats weighing 1.5 to 3.0 Kg were compulsorily infected with $10^4$ $TCID_{50}$ of FHV-1-K1 strain through nose. At the second day, 30 and 10 mg/Kg of FH2 was administered via the jugular vein. General clinical conditions such as weight, temperature, an amount of taking meals, an amount of drinking water and spirits, and respiratory lesions such as tears, conjunctivitis, rhinorrhea, sneeze and cough were observed with the lapse of time and scored as 0 for no symptom, 1 for light symptom, 2 for moderate symptom and 3 for severe symptom. As a result, both groups administered with 10 and 30 mg/kg alleviated the symptoms (FIG. 11). Then, SPF cats weighing 1.4 to 2.3 kg were compulsorily infected with $10^4$ $TCID_{50}$ of FHV-1-K1 strain. At the second day, 30 and 10 mg/kg of FH2 were administered via the jugular vein and the clinical conditions were observed. As a result, the onset of the symptoms were inhibited in the group administered with FH2 (FIG. 12). These showed the in vivo usefulness of FH2 against FHV infection.

In addition, after administration of FH2, no side effect such as diarrhea, vomiting or another shock-like symptom was observed, and hence, the safety of FH2 was confirmed.

From the above-mentioned point of view, FH2 antibody can be applied as diagnostic, treating and preventing agents effective against FHV-1 infection with no side effect.

Industrial Applicability of the Invention

The feline monoclonal antibody of the present invention is effective against feline virus herpes virus-1 infection and is applicable as diagnostic, treating and preventing agents against said disease.

We claim:

1. A felinized chimeric antibody having a heavy chain variable region (VH) and a light chain variable region (VL) obtained from a murine antibody, which specifically reacts with feline herpes virus-1 (FHV-1) and has a neutralizing activity against FHV-1, wherein the amino acid sequence of one of the complementarity determining regions (CDRs) of heavy chain variable region (VH) has the amino acid sequence Asp Gly Ala Trp Phe Pro Phe (corresponding to amino acid residues 126 to 132 of SEQ ID NO:2) and the amino acid sequences of the constant (C) regions of the heavy (H) and light (L) chains are those obtained from a feline antibody.

2. The antibody of claim 1 wherein the CDRs in said VH and VL regions have the following amino acid sequences:
VH:
CDR1: LeuSerThrSerGlyMetGlyAlaGly corresponding to amino acids 48 to 56 of SEQ ID NO:2;
CDR2: HisIleTrpTrpAspAspValLysArg-TyrAsnProAlaLeuLysSer corresponding to amino acids 71 to 86 of SEQ ID NO:2;
CDR3: SerGlnIleTyrPheAspTyrAspGly-AlaTrpPheProPhe corresponding to amino acids 119 to 132 of SEQ ID NO:2; VL:
CDR1: ArgAlaSerGlnSerIleSerAsnAsnLeuHis corresponding to amino acids 44 to 54 of SEQ ID NO:4;
CDR2: AlaSerGlnSerIleSerGly corresponding to amino acids 71 to 77 of SEQ ID NO:4; and
CDR3: GlnGlnSerAsnSerTrpProHisThr corresponding to amino acids 109 to 117 of SEQ ID NO:4.

3. The antibody of claim 1 wherein said VH and VL regions have the amino acid sequences of amino acid residues 20 to 143 in SEQ ID NO:2 and of amino acid residues 21 to 127 in SEQ ID NO:4, respectively.

4. The antibody of claim 1 wherein the amino acid sequence of the H chain constant region of said antibody is that of SEQ ID NO:6 and the amino acid sequence of the L chain constant region of said antibody is that of SEQ ID NO:8 or of SEQ ID NO:10.

5. A gene fragment coding for a heavy chain variable region (VH) or a part thereof of an antibody which specifically reacts with feline herpes virus-1 (FHV-1) in which the nucleotide sequence coding for complementarity determining region 3 (CDR3) comprises a nucleotide sequence coding for the amino acid sequence Asp Gly Ala Trp Phe Pro Phe corresponding to amino acid residues 126 to 132 of SEQ ID NO:2.

6. The gene fragment of claim 5 wherein the nucleotide sequences coding for CDRs 1 to 3 are nucleotide sequences coding for the following amino acid sequences, respectively:
CDR1: LeuSerThrSerGlyMetGlyAlaGly corresponding to amino acids 48 to 56 of SEQ ID NO:2.
CDR2: HisIleTrpTrpAspAspValLysArg-TyrAsnProAlaLeuLysSer corresponding to amino acids 71 to 86 of SEQ ID NO:2.
CDR3: SerGlnIleTyrPheAspTyrAspGly-AlaTrpPheProPhe corresponding to amino acids 119 to 132 of SEQ ID NO:2.

7. The gene fragment of claim 5 wherein the nucleotide sequence coding for VH of the antibody is a nucleotide sequence coding for the amino acid sequence of SEQ ID NO:2.

8. The gene fragment of claim 5 wherein the nucleotide sequence coding for VH of the antibody is the corresponding to nucleotides 21 to 449 of SEQ ID NO:1.

9. A gene fragment coding for a light chain variable region (VL) of an antibody wherein the nucleotide sequences coding for CDRs 1 to 3 are nucleotide sequences coding for the following amino acid sequences, respectively:
CDR1: ArgAlaSerGlnSerIleSerAsnAsnLeuHis corresponding to amino acids 44 to 54 of SEQ ID NO:4;
CDR2: AlaSerGlnSerIleSerGly corresponding to amino acids 71 to 77 of SEQ ID NO:4 and
CDR3: GlnGlnSerAsnSerTrpProHisThr corresponding to amino acids 109 to 117 of SEQ ID NO:4.

10. The gene fragment of claim 9 wherein the nucleotide sequence coding for VL of the antibody is a nucleotide sequence coding for the amino acid sequence of SEQ ID NO:4.

11. The gene fragment of claim 9 wherein the nucleotide sequence coding for VL of the antibody is the nucleotide corresponding to nucleotides 23 to 403 of SEQ ID NO:3.

12. A recombinant gene fragment coding for heavy (H) chain of a feline chimeric antibody which specifically reacts with feline herpes virus-1 (FHV-1), said gene fragment comprising the gene fragment of claim 5 to the downstream (3' site) of which a gene fragment coding for H chain constant region of a feline antibody is bound.

13. The recombinant gene fragment of claim 12 wherein said gene fragment coding for H chain constant region of a feline antibody has a nucleotide sequence coding for the amino acid sequence of SEQ ID NO:6.

14. A recombinant gene fragment coding for light (L) chain of a feline chimeric antibody which specifically reacts with feline herpes virus-1 (FHV-1), said gene fragment comprising the gene fragment of claim 9 to the downstream (3' site) of which a gene fragment coding for κ chain constant region of a feline antibody is bound.

15. The recombinant gene fragment of claim 14 wherein said gene fragment coding for κ chain constant region of a feline antibody has a nucleotide sequence coding for the amino acid sequence of SEQ ID NO:8.

16. A recombinant gene fragment coding for L chain of a feline chimeric antibody which specifically reacts with feline herpes virus-1 (FHV-1), said gene fragment comprising the gene fragment of claim 9 to the downstream (3' site) of which a gene fragment coding for λ chain constant region of a feline antibody is bound.

17. The recombinant gene fragment of claim 16 wherein said gene fragment coding for λ chain constant region of a feline antibody has a nucleotide sequence coding for the amino acid sequence of SEQ ID NO:10.

18. A method of treating FHV-1-infected cats, comprising the step of administering a pharmaceutical composition, comprising the felinized chimeric antibody according to claim 2 and a pharmaceutically acceptable excipient, to a cat in need thereof.

* * * * *